United States Patent
Gephart

(10) Patent No.: US 10,881,437 B2
(45) Date of Patent: Jan. 5, 2021

(54) BONE PLATE SYSTEM AND METHOD

(71) Applicant: A&E Advanced Closure Systems, LLC, Los Angeles, CA (US)

(72) Inventor: Matthew P. Gephart, Marquette, MI (US)

(73) Assignee: A&E Advanced Closure Systems, LLC, Los Angeles, CA (US)

( * ) Notice: Subject to any disclaimer, the term of this patent is extended or adjusted under 35 U.S.C. 154(b) by 197 days.

(21) Appl. No.: 16/011,039

(22) Filed: Jun. 18, 2018

(65) Prior Publication Data

US 2018/0296259 A1 Oct. 18, 2018

Related U.S. Application Data

(63) Continuation of application No. 14/562,542, filed on Dec. 5, 2014, now Pat. No. 9,999,454.

(60) Provisional application No. 61/912,246, filed on Dec. 5, 2013.

(51) Int. Cl.
*A61B 17/80* (2006.01)
*A61B 17/82* (2006.01)

(52) U.S. Cl.
CPC ............ *A61B 17/80* (2013.01); *A61B 17/808* (2013.01); *A61B 17/82* (2013.01)

(58) Field of Classification Search
CPC .... A61B 17/80; A61B 17/808; A61B 17/8004
See application file for complete search history.

(56) References Cited

U.S. PATENT DOCUMENTS

| | | | |
|---|---|---|---|
| 1,988,534 A | 1/1935 | Abbott |
| 2,002,977 A | 5/1935 | Carr |
| 2,557,877 A | 6/1951 | Kluson |
| 3,959,960 A | 6/1976 | Santos |
| 4,050,464 A | 9/1977 | Hall |
| 4,184,784 A | 1/1980 | Killian |
| 4,269,180 A | 5/1981 | Dall |

(Continued)

FOREIGN PATENT DOCUMENTS

| AU | 743254 | 12/2000 |
|---|---|---|
| CN | 201260694 Y | 6/2009 |

(Continued)

OTHER PUBLICATIONS

U.S. Appl. No. 15/411,682, filed Jan. 20, 2017, Robert A. Goodwin, Jr.

(Continued)

*Primary Examiner* — Christopher J Beccia
(74) *Attorney, Agent, or Firm* — Fitch, Even, Tabin & Flannery LLP

(57) ABSTRACT

A bone plate system is provided that permits rapid, secure stabilization of a plurality of bones, such as portions of a cut rib. The bone plate system includes a bone plate having anchor devices for securing the bone plate to, for example, cortical bone of the cut rib portions. The anchor devices have an open configuration that permits the anchor devices to be connected to the cortical bone of the cut rib portions and a clamping configuration that fixes the bone plate to the cortical bone of the cut portions. The bone plate connects the cut rib portions and stabilizes the cut rib portions against relative movement therebetween.

26 Claims, 42 Drawing Sheets

(56) References Cited

U.S. PATENT DOCUMENTS

| | | | |
|---|---|---|---|
| 4,327,715 A | 5/1982 | Corvisier | |
| 4,583,541 A | 4/1986 | Barry | |
| 4,959,065 A | 9/1990 | Arnett | |
| 4,966,600 A | 10/1990 | Songer | |
| 5,015,248 A | 5/1991 | Burstein | |
| 5,139,498 A | 8/1992 | Astudillo Ley | |
| 5,312,410 A | 5/1994 | Miller | |
| 5,395,374 A | 3/1995 | Miller | |
| 5,415,658 A | 5/1995 | Kilpela | |
| 5,449,361 A | 9/1995 | Preissman | |
| 5,456,722 A | 10/1995 | McLeod | |
| 5,514,091 A | 5/1996 | Yoon | |
| 5,522,827 A | 6/1996 | Combs | |
| 5,536,270 A | 7/1996 | Songer | |
| 5,541,380 A | 7/1996 | Ogden | |
| 5,568,865 A | 10/1996 | Mase | |
| 5,569,253 A | 10/1996 | Farris | |
| 5,578,057 A | 11/1996 | Wenstrom, Jr. | |
| 5,649,927 A | 7/1997 | Kilpela | |
| 5,660,091 A | 8/1997 | Stone | |
| 5,665,089 A * | 9/1997 | Dall | A61B 17/80 606/309 |
| 5,702,399 A | 12/1997 | Kilpela | |
| 5,752,959 A | 5/1998 | Korhonen | |
| 5,755,704 A | 5/1998 | Lunn | |
| 5,810,825 A | 9/1998 | Huebner | |
| 5,849,012 A | 12/1998 | Abboudi | |
| 5,902,305 A | 5/1999 | Beger | |
| 5,908,421 A | 6/1999 | Beger | |
| 5,935,130 A | 8/1999 | Kilpela | |
| 5,935,133 A | 8/1999 | Wagner | |
| 5,941,881 A | 8/1999 | Barnes | |
| 6,017,347 A | 1/2000 | Huebner | |
| 6,077,268 A | 6/2000 | Farris | |
| 6,086,590 A | 7/2000 | Margulies | |
| 6,099,527 A | 8/2000 | Hochschuler | |
| 6,120,506 A | 9/2000 | Kohrs | |
| 6,123,709 A | 9/2000 | Jones | |
| 6,277,120 B1 | 8/2001 | Lawson | |
| 6,342,068 B1 | 1/2002 | Thompson | |
| 6,378,289 B1 | 4/2002 | Trudeau | |
| 6,387,099 B1 | 5/2002 | Lange | |
| 6,398,787 B1 | 6/2002 | Itoman | |
| 6,399,886 B1 | 6/2002 | Avellanet | |
| 6,454,770 B1 | 9/2002 | Klaue | |
| 6,475,220 B1 | 11/2002 | Whiteside | |
| 6,494,907 B1 | 12/2002 | Bulver | |
| 6,520,965 B2 * | 2/2003 | Chervitz | A61B 17/842 606/103 |
| 6,575,913 B1 | 6/2003 | Woolley | |
| 6,605,091 B1 | 8/2003 | Iwanski | |
| 6,629,975 B1 | 10/2003 | Kilpela | |
| 6,730,091 B1 | 5/2004 | Pfefferle | |
| 6,832,532 B2 | 12/2004 | Kilpela | |
| 6,872,210 B2 | 3/2005 | Hearn | |
| 7,052,499 B2 | 5/2006 | Steger | |
| 7,156,847 B2 | 1/2007 | Abramson | |
| 7,207,993 B1 | 4/2007 | Baldwin | |
| 7,229,444 B2 | 6/2007 | Boyd | |
| 7,250,054 B2 | 7/2007 | Allen | |
| 7,494,461 B2 | 2/2009 | Wells | |
| 7,635,365 B2 | 12/2009 | Ellis | |
| 7,695,501 B2 | 4/2010 | Ellis | |
| 7,785,355 B2 | 8/2010 | Mohr | |
| 7,803,176 B2 | 9/2010 | Teague | |
| 8,282,675 B2 | 10/2012 | Maguire | |
| 8,298,247 B2 | 10/2012 | Sterrett | |
| 8,313,517 B2 | 11/2012 | Mohr | |
| 8,337,497 B2 | 12/2012 | Deslauriers | |
| 8,372,123 B2 | 2/2013 | Smisson, III | |
| 8,460,295 B2 | 6/2013 | McClellan | |
| 8,460,345 B2 | 6/2013 | Steger | |
| 8,783,671 B2 | 7/2014 | Ranieri | |
| 8,840,735 B2 | 9/2014 | Schaffer | |
| 8,984,720 B2 | 3/2015 | Gephart | |
| 9,265,543 B2 | 2/2016 | Gephart | |
| 9,333,021 B2 | 5/2016 | Gephart | |
| 9,510,822 B2 | 12/2016 | Poucher | |
| 9,510,882 B2 | 12/2016 | Dell'Oca | |
| 9,561,064 B2 | 2/2017 | Goodwin | |
| 2002/0072753 A1 | 6/2002 | Cohen | |
| 2002/0177861 A1 | 11/2002 | Sugiyama | |
| 2003/0153947 A1 | 8/2003 | Koseki | |
| 2004/0138666 A1 | 7/2004 | Molz | |
| 2004/0199169 A1 | 10/2004 | Koons | |
| 2005/0171547 A1 | 8/2005 | Aram | |
| 2005/0177179 A1 | 8/2005 | Baynham | |
| 2006/0089646 A1 | 4/2006 | Bonutti | |
| 2006/0155328 A1 | 7/2006 | Foerster | |
| 2006/0167464 A1 | 7/2006 | Allen | |
| 2006/0271060 A1 | 11/2006 | Gordon | |
| 2006/0287653 A1 | 12/2006 | Rhyne | |
| 2007/0225715 A1 | 9/2007 | Deffenbaugh | |
| 2008/0195145 A1 | 8/2008 | Bonutti | |
| 2008/0275477 A1 | 11/2008 | Sterrett | |
| 2008/0287951 A1 | 11/2008 | Stoneburner | |
| 2008/0306553 A1 | 12/2008 | Zucherman | |
| 2009/0043316 A1 | 2/2009 | Durgin | |
| 2009/0054933 A1 | 2/2009 | Mickiewicz | |
| 2009/0069812 A1 | 3/2009 | Gillard | |
| 2009/0069851 A1 | 3/2009 | Gillard | |
| 2009/0105717 A1 | 4/2009 | Bluechel | |
| 2009/0171402 A1 | 7/2009 | Dell Oca | |
| 2010/0042106 A1 | 2/2010 | Bryant | |
| 2010/0057091 A1 | 3/2010 | Oosterom | |
| 2010/0094294 A1 | 4/2010 | Gillard | |
| 2010/0094362 A1 | 4/2010 | Lutze | |
| 2010/0121387 A1 | 5/2010 | Belliard | |
| 2010/0179595 A1 | 7/2010 | Jackson | |
| 2010/0305571 A1 | 12/2010 | Pratt | |
| 2010/0318137 A1 | 12/2010 | Stucki | |
| 2010/0331844 A1 | 12/2010 | Ellis | |
| 2010/0331892 A1 | 12/2010 | Fell | |
| 2011/0079315 A1 | 4/2011 | Norton | |
| 2011/0112537 A1 | 5/2011 | Bernstein | |
| 2011/0218580 A1 | 9/2011 | Schwager | |
| 2011/0224676 A1 | 9/2011 | Dell Oca | |
| 2011/0319978 A1 | 12/2011 | Schaffer | |
| 2012/0016384 A1 | 1/2012 | Wilke | |
| 2012/0059418 A1 * | 3/2012 | Denham | A61B 17/8869 606/232 |
| 2012/0089193 A1 | 4/2012 | Stone | |
| 2012/0215224 A1 | 8/2012 | Songer | |
| 2012/0226321 A1 | 9/2012 | Gonzalez-Hernandez | |
| 2012/0303065 A1 | 11/2012 | Larroque-Lahitette | |
| 2013/0167334 A1 | 7/2013 | Gephart | |
| 2013/0289564 A1 | 10/2013 | Bernstein | |
| 2013/0331897 A1 | 12/2013 | Holt | |
| 2014/0058445 A1 | 2/2014 | Mattchen | |
| 2014/0088688 A1 | 3/2014 | Lilburn | |
| 2014/0142638 A1 | 5/2014 | Goodwin | |
| 2014/0243907 A1 * | 8/2014 | Cavallazzi | A61B 17/74 606/286 |
| 2015/0127003 A1 | 5/2015 | Songer | |
| 2015/0182674 A1 | 7/2015 | Schaffer | |
| 2015/0342654 A1 | 12/2015 | Gephart | |
| 2016/0174997 A1 | 6/2016 | Spitznagel | |
| 2016/0331431 A1 | 11/2016 | Gephart | |
| 2017/0071648 A1 | 3/2017 | Dell'Oca | |
| 2017/0143394 A1 | 5/2017 | Goodwin | |
| 2017/0209190 A1 | 7/2017 | Goodwin, Jr. | |
| 2018/0029824 A1 | 2/2018 | Gephart | |

FOREIGN PATENT DOCUMENTS

| | | |
|---|---|---|
| DE | 7707950 U | 4/1978 |
| TW | 314764 | 9/1997 |
| WO | 9400063 | 1/1994 |
| WO | 9428812 | 12/1994 |
| WO | 200149191 | 7/2001 |
| WO | 0234120 | 5/2002 |
| WO | 2006088452 | 8/2006 |
| WO | 2011041624 | 4/2011 |
| WO | 2011116364 | 9/2011 |

(56) References Cited

FOREIGN PATENT DOCUMENTS

| WO | 2013003719 | 1/2013 |
| WO | 2014140100 | 9/2014 |
| WO | 2017127692 | 7/2017 |

OTHER PUBLICATIONS

U.S. Appl. No. 15/645,029, filed Jul. 10, 2017, Gephart.
U.S. Appl. No. 62/286,062, filed Jan. 22, 2016, Robert A. Mitchell.
U.S. Appl. No. 62/368,753, filed Jul. 29, 2016, Matthew P. Gephart.
Acute Innovation—Quick and Easy Installation & Re-entry, Acute Innovation, LLC, htto://www.acuteinnovations.com/oroducts/AcuTie/Installtion, May 16, 2012, 7 pages.
Ease of Wre with the Stability of a Plate, AcuTie Sternal Closure System, Oct. 2010, 12 pages.
Re-Entry Options, AcuTie Sternal Closure System, accessed May 16, 2012, 1 page.
Sternalock Blu Primary Closure System, Biomet Microfixation, Form No. BMF00-3265, Rev 05k1110, 2011, 10 pages.
Technique Guide, Modular Sternal Cable System Flexibility and Strength in Sternal Closure and Repair, Synthes CMF, Jul. 2008, 39 pages.
Technique Guide, Titanium Sternal Fixation System for Stable Internal Fixation of the Sternum, Synthes, Inc., Oct. 2010, 36 pages.

\* cited by examiner

BONE PLATE SYSTEM AND METHOD

CROSS-REFERENCE TO RELATED APPLICATIONS

This application is a continuation of U.S. patent application Ser. No. 14/562,542, filed Dec. 5, 2014, which claims the benefit of U.S. Provisional Application No. 61/912,246, filed Dec. 5, 2013, which are each hereby incorporated by reference in their entirety herein.

FIELD OF THE INVENTION

The invention relates to bone plate systems and, more particularly, to bone plate systems for stabilizing one or more bones.

BACKGROUND OF THE INVENTION

There are presently many different types of bone plate systems for securing bones so that the secured bones may fuse or heal. As used herein, the term bone may refer to a bone, a bone fragment, or a portion of a bone. One application for bone plate systems is for securing broken or fractured bones so that they may fuse together. Another application for bone plate systems is securing cut bones, such as during a thoracotomy. A thoracotomy may involve cutting one or more ribs and, in some instances, removing a section of one or more ribs in order to provide access to tissues and organs within the chest cavity of a patient.

After the tissues or organs within the chest cavity have been operated upon, the cut rib(s) of the patient may be repaired. For example, if one rib has been cut, a bone plate and screws may be used to secure the portions of the cut rib together. However, ribs are relatively thin and consist of soft cancellous bone enclosed in a thin, compact layer of hard cortical bone. Driving the screws of the bone plate into the portions of the cut rib exerts an outward pressure upon the bone which may splinter the bone. Further, in order to achieve sufficient purchase in the bone, the screws may need to be driven completely through both layers of cortical bone and the cancellous bone therebetween. This may cause a portion of a screw shank to extend beyond the rib and irritate tissues within the chest cavity.

Another problem is that each rib has a delicate neurovascular bundle of a vein, an artery, and a nerve extending along the underside of the rib. The presence of the neurovascular bundle on the underside of a rib further complicates the placement of bone plate systems after the rib has been broken or cut.

DETAILED DESCRIPTION OF THE PREFERRED EMBODIMENTS

Figure 1:
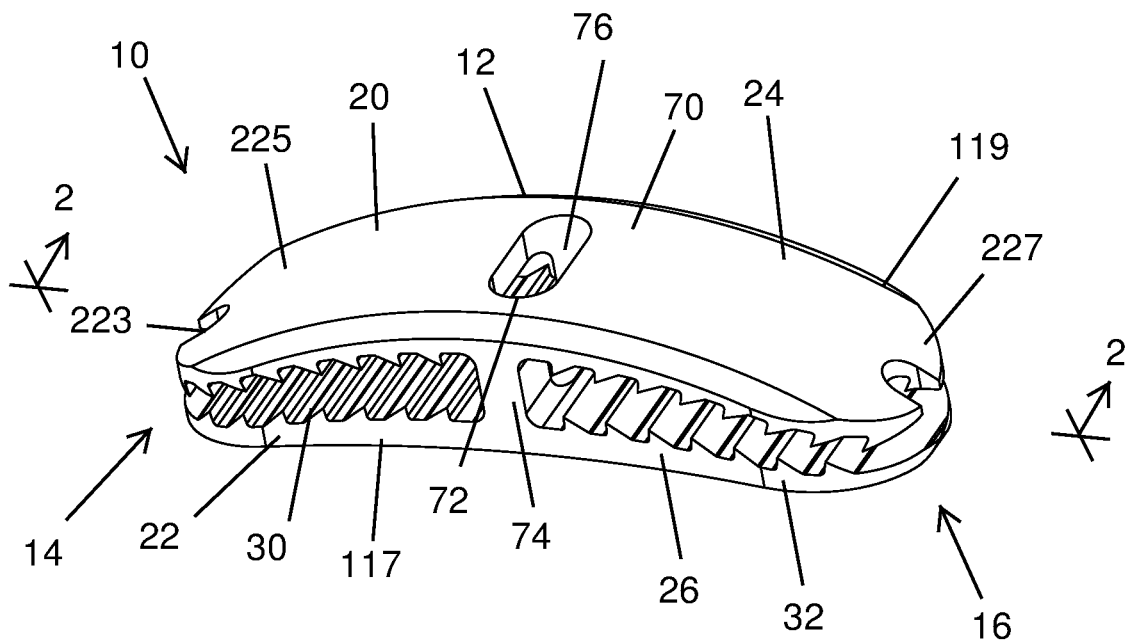
FIG. 1 is a perspective view of a bone plate system including a bone plate having pairs of jaws.
Figure 2:
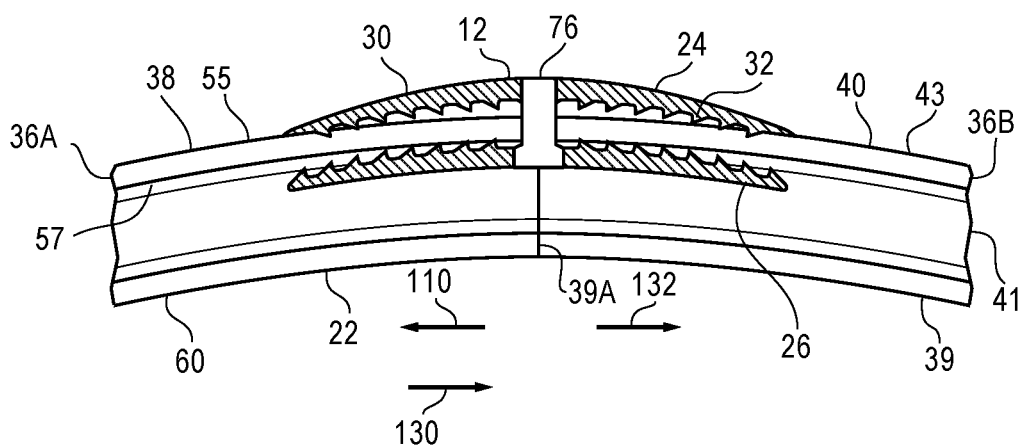
FIG. 2 is a cross-sectional view taken across line 2-2 in FIG. 1 showing the bone plate securing two portions of a cut rib together.
Figure 10:
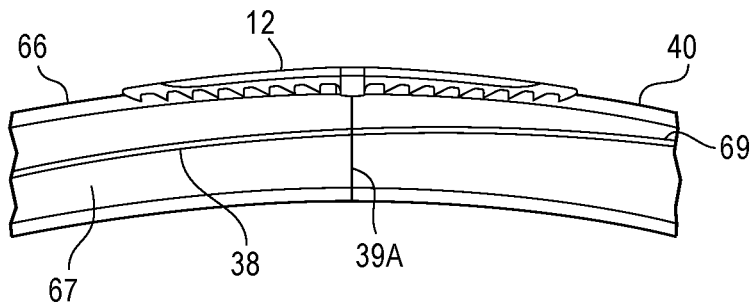
FIG. 10 is a side elevational view of the bone plate system of FIG. 1 showing the bone plate securing rib portions and teeth of the bone plate engaged with exterior surfaces of the rib portions.
Figure 11:
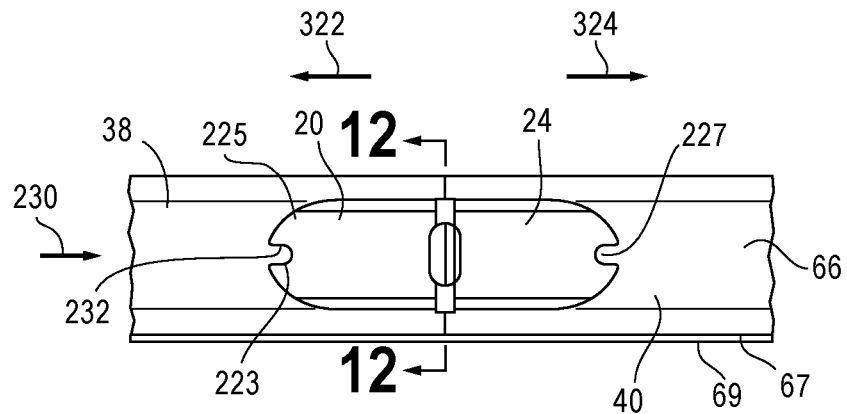
FIG. 11 is a top plan view of the bone plate and rib portions of FIG. 10 showing openings at tips of the bone plate jaws for engaging the studs of the inserter tool levers.

With respect to FIGS. 1 and 2, a bone plate system 10 is provided that permits rapid, secure stabilization of a plurality of bone portions, such as portions 38, 40 of rib 39 separated by a break or cut 39A. The bone plate system 10 includes a bone plate 12 and anchor devices 14, 16 of the bone plate 12 configured to secure the bone plate 12 to the rib portions 38, 40. The anchor devices 14, 16 include pairs of upper and lower jaws 20, 22 and 24, 26 having teeth 30, 32 configured to clamp onto cortical bones 36A, 36B of the rib portions 38, 40. In one form, the bone plate 12 and jaws 20, 22, 24, 26 are formed integrally from a resilient material, such as super elastic nitinol. The resilient properties of the bone plate 12 bias the jaws 20, 22 and 24, 26 together once the jaws 20, 22 and 24, 26 have been deflected away from each other and positioned on the cortical bones 36A, 36B. This biasing due to the resilient properties of the bone plate 12 engages the teeth 30, 32 with the cortical bones 36A, 36B and secures the bone plate 12 to the cortical bones 36A, 36B. The bone plate 12 thereby extends across the cut 39A and secures the cut rib portions 38, 40 together by forming a rigid connection between the cortical bones 36A, 36B, which are typically the strongest sections of the cut rib portions 38, 40. With reference to FIGS. 10 and 11, the bone plate 12 has a small footprint on an anterior surface 66 of the rib sections 38, 40 which minimizes irritation to surrounding tissues. Further, the bone plate 12 does not contact or extend across an underside 67 of the rib sections 38, 40 which limits interference with the neurovascular bundle 69 thereon.

Figure 3:
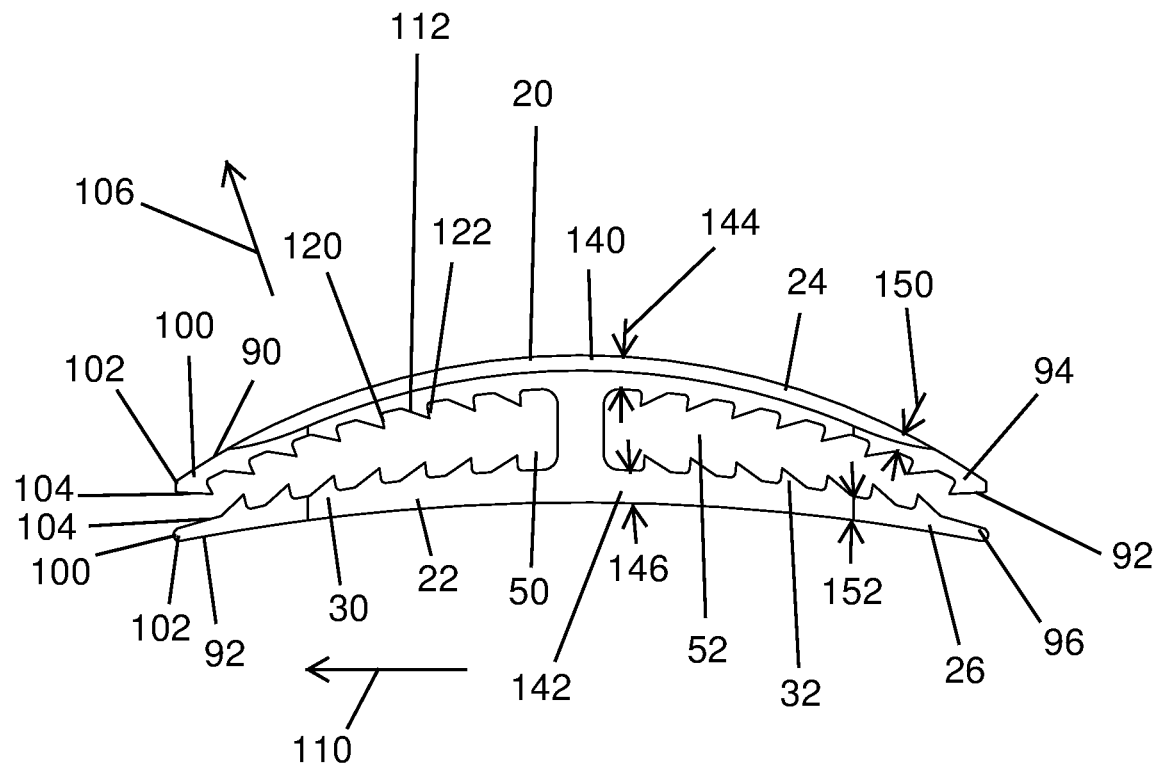
FIG. 3 is a front elevational view of the bone plate of FIG. 1 showing the jaws of the bone plate in an initial, undeflected configuration.
Figure 4:
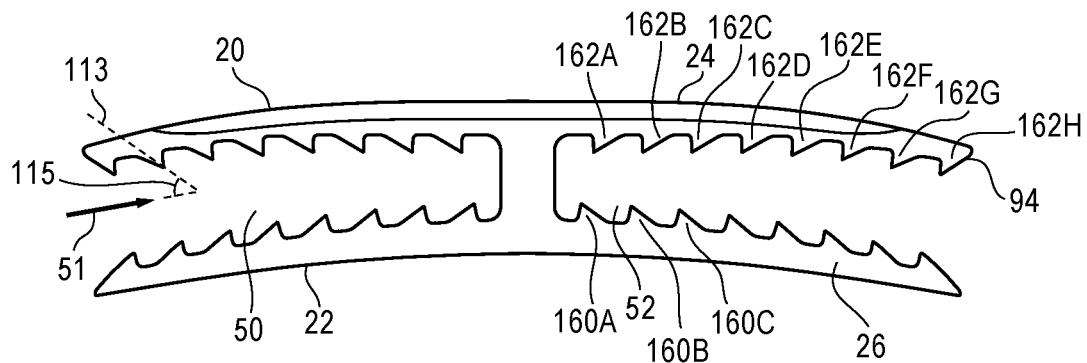
FIG. 4 is a front elevational view similar to FIG. 3 showing the jaws of the bone plate in a deflected, open configuration.
Figure 4A:
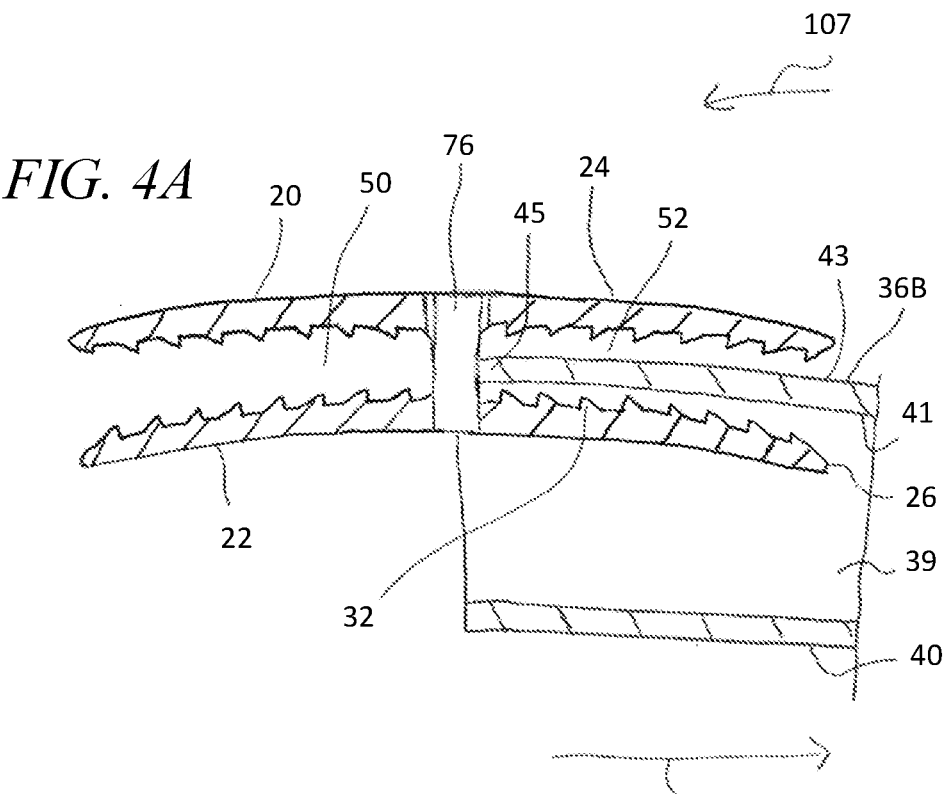
FIGS. 4A and 4B are cross-sectional views similar to FIG. 2 showing the bone plate being connected to the rib portions.
Figure 4B:
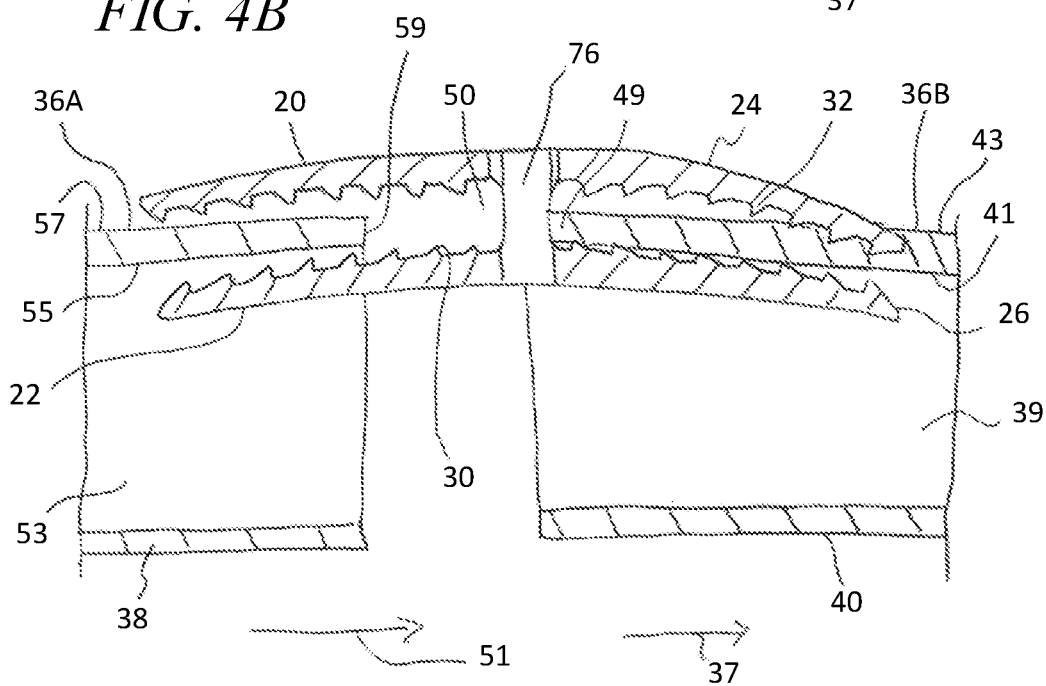

With reference to FIGS. 4-4B, the bone plate 12 is connected to each of the rib portions 38, 40 using a process similar to attaching a binder clip to a stack of papers. More specifically, a user shifts one or both of the upper and lower jaws 24, 26 to reconfigure the jaws 24, 26 from an undeflected, initial configuration (see FIG. 3) to a deflected, open configuration (see FIG. 4) which widens a bone receiving gap 52 between the jaws 24, 26. The bone plate 12 is then advanced in direction 37 so that the lower jaw 26 travels into an intramedullary canal 39 of the rib section 40 along an inner surface 41 of the cortical bone 36B and the upper jaw 24 travels outside of the rib section 40 along an outer surface 43 of the cortical bone 36B, as shown in FIG. 4A. In one approach, a trocar may be inserted into the intramedullary canal 39 to remove or reposition cancellous bone within the intramedullary canal 39. The bone plate 12 is advanced in direction 37 until an end 45 of the cortical bone 36B abuts supports 74, 76 of the bone plate (see FIG. 1). Next, the one or both deflected jaws 24, 26 are released that permits the one or more jaws 24, 26 to shift to a less deflected, clamping configuration which narrows the bone receiving gap 52 between the jaws 24, 26, as shown in FIG. 4B. This clamps the jaws 24, 26 onto the cortical bone 36B and tightly engages the teeth 32 with the inner and outer surfaces 41, 43 of the cortical bone 36B. In one approach, the jaws 24, 26 are configured to clamp the cortical bone 36B with 60 lbs of force.

The jaws 20, 22 are fixed to the cortical bone 36A using a process similar to the process of fixing the jaws 24, 26 to the cortical bone 36B. With reference to FIG. 4B, one or both of the jaws 20, 22 are deflected away from the other jaw 20, 22 to reconfigure the jaws 20, 22 from an undeflected, initial configuration to a deflected, open configuration which expands a bone receiving gap 50 between the jaws 20, 22. With the jaws 20, 22 in the open configuration, the cortical bone 36A of rib section 38 is advanced in direction 51 into the bone-receiving gap 50 so that the lower jaw 22 travels into an intramedullary canal 53 of the rib section 38 and along an inner surface 55 of the cortical bone 36A while the upper jaw 24 travels along an outer surface 57 of the rib section 38. The rib section 38 is advanced in direction 51 until an end 59 of the cortical bone 36A abuts the supports 74, 76. (In one approach, the cortical bone ends 45, 59 are notched during surgery to receive the supports 74, 76 and minimize the gap between the cortical bone ends 45, 59 caused by the presence of the bone plate 12.) Next, the one or both jaws 20, 22 are released which permits the one or more jaws 20, 22 to shift to an intermediate (and less deflected) clamping configuration which narrows the bone receiving gap 50 between the jaws 20, 22. As shown in FIG. 2, this clamps the jaws 20, 22 onto the cortical bone 36A and tightly engages the teeth 30 with the inner and outer surfaces 55, 57 of the cortical bone 36A. In this manner, the bone plate 12 may be fixed to the cortical bones 36A, 36B to stabilize the rib sections 38, 40.

Figure 12:
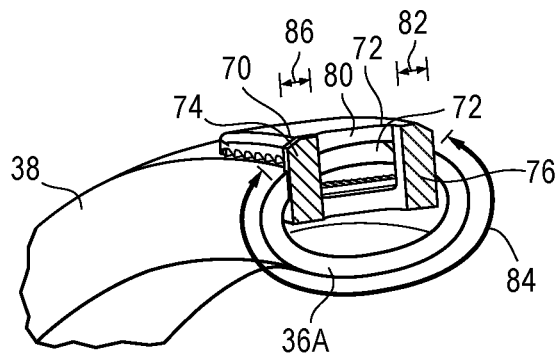
FIG. 12 is cross-sectional view taken across line 12-12 in FIG. 11 showing a large, unobstructed surface area of cortical bone of the rib portion for fusing with the cortical bone of the other rib portion.

With reference to FIGS. 1 and 3, the bone plate 12 has a body 70 with a bone growth window 72 therein that permits cortical bone growth between the ends 45, 59 of the ribs sections 38, 40 (see FIG. 2). The body 70 includes the supports 74, 76 extending between the upper jaws 20, 24 and lower jaws 22, 24. With reference to FIG. 12, the supports 74, 76 are on opposite sides of the window 72 which provides a cortical bone growth area 80 therebetween. The cortical bone growth area 80 permits the cortical bone 36A, 36B to fuse together through the bone plate window 72 which further secures the bone plate 12 to the rib sections 38, 40. Further, the cortical bones 36A, 36B may fuse together post-operatively along end surface area 84 of the rib sections 38, 40, as shown in FIG. 12. The bone plate 12 thereby maximizes the ability of the cortical bones 36A, 36B to fuse together while obstructing cortical bone growth in only small areas 82, 86 at the supports 74, 76. In one approach, the bone plate 12 obstructs only 20% of the end surface area 84 of the cortical bone sections 36A, 36B and permits the remaining 80% of the end surface area 84 of the sections 36A, 36B to fuse together post-operatively.

With reference to FIGS. 3 and 4 the bone plate 12 has features that increase the ease with which the bone plate 12 may be applied to the cortical bones 36A, 36B of the rib sections 38, 40. The jaws 20, 22 and 24, 26 have tips 90, 92, 94, 96 each including a leading end 100 configured to engage the end 45 or 59 of the cortical bones 36A, 36B (see FIG. 2) and shift the associated jaw 20, 22, 24, or 26 away from the cortical bone 36A, 36B. For example, the end 100 of the jaw 20 has a rounded outer surface 102 extending inward toward an inclined surface 104. The rounded outer surface 102 contacts the end 59 of the cortical bone 36A and the inclined surface 104 shifts the jaw 20 upward in direction 106 as the cortical bone 36A is advanced in direction 51 into the gap 50 between the jaws 20, 22 (see FIG. 4B). In this manner, the inclined surface 104 may operate as a cam surface that translates the linear movement of the cortical bone 36A along the gap 50 into outward deflection of the jaw 20. The outward deflection of the jaw 20 widens the gap 50 and permits the cortical bone 36A to be advanced farther into the gap 50 toward the supports 74, 76. With reference to FIG. 3, the leading end 100 of the jaw 22 also has an outer curved surface 102 and an inclined surface 104 configured to contact the end 59 of cortical bone 36A and shift the jaw 22 outwardly away from the jaw 20 in a manner similar to the leading end 100 of the jaw 20. It will be appreciated that one or both of the jaws 20, 22 may be shifted outwardly during positioning of the jaws 20, 22 on the cortical bone 36A depending on, for example, the thickness of the cortical bone 36A and/or the approach angle of the jaws 20, 22.

With reference to FIGS. 1 and 3, another feature of the bone plate 12 that increase the ease with which the bone plate 12 may be applied to the cortical bones 36A, 36B are ramp surfaces 112 of the teeth 30. Each tooth 30 and ramp surface 112 thereof extends from one side 117 (see FIG. 1) of the bone plate 12 to another side 119 of the bone plate 12 with a generally triangular cross-section. With respect to FIG. 4, the ramp surface 112 extends along a plane 113 oriented at an acute angle 115 relative to the direction 51 in which the cortical bone 36A is advanced into the bone-receiving gap 50. Each ramp surface 112 is configured to engage the cortical bone 36A as the cortical bone end 59 is advanced in direction 51 into the bone-receiving gap 50 between the jaws 20, 22. The ramp surface 112 causes the respective tooth 30 and associated jaw 20 or 22 to shift away from the cortical bone 36A as the cortical bone 36A engages and travels along the ramp surface 112. Thus, one or both of the jaws 20, 22 are shifted apart due to engagement of the inclined surfaces 104 and ramp surfaces 112 with the cortical bone 36 which expands the gap 50 and permits the cortical bone 36A to travel farther into the gap 50.

Once the cortical bone end 59 has been advanced into abutting contact with the supports 74, 7, the resilient properties of the bone plate 12 bias the one or both previously-shifted jaws 20, 22 toward the clamping configuration which clamps the jaws 20, 22 against the cortical bone 36A, as shown in FIG. 2. This drives points 120 of the teeth 30 (see FIG. 3) into the internal and external surfaces 55, 57 of the cortical bone 36A and fixes the jaws 20, 22 to the cortical bone 36A, as shown in FIG. 2. The teeth 30 each also have a stop surface 122 oriented transverse to a withdrawal direction 110 for the rib section 38, as shown in FIG. 3. As the teeth points 120 dig into the interior and exterior surfaces 55, 57 of the cortical bone 36A, the stop surface 122 engage the cortical bone 36A near the points 120 and resist movement of the cortical bone 36A in direction 110 outward from the bone-receiving gap 50 between the jaws 20, 22. Thus, whereas the ramp surface 112 of each tooth 30 facilitates advancing of the cortical bone 36A in direction 51 between the jaws 20, 22 (see FIG. 4B), the point 120 and stop surface 122 bite into the cortical bone 36A and restrict movement of the cortical bone 36A in withdrawal direction 110 (see FIG. 2) once the one or more jaws 20, 22 have resiliently shifted toward the clamping configuration.

Further, the jaws 24, 26 have teeth 32 and tips 94, 96 with shapes similar to the jaws 20, 22 and which function similarly to facilitate connecting of the jaws 24, 26 to the cortical bone 36B. However, with reference to FIGS. 2 and 4A, the teeth 32 are configured and arranged to permit the cortical bone 36B to be advanced in direction 107 (which is opposite to direction 51, see FIG. 4B) between the jaws 24, 26 while fixing the jaws 24, 26 to the cortical bone 36A and restricting movement of the cortical bone 36A in withdrawal direction 37 (which is opposite to direction 110) outward from between the jaws 24, 26. The opposite retention forces produced by the jaws 20, 22 and 24, 26 once fixed to the cortical bones 36A, 36B resists the rib sections 38, 40 from moving apart post-operatively, such as movement due to the patient's breathing.

It will be appreciated that the teeth 30, 32 may take a variety of forms and may be adapted for particular applications. For example, the teeth 30, 32 may include rows of smaller, spaced teeth rather than a single tooth extending between the sides 117, 119 of the bone plate 12. As another example, the teeth 30, 32 may have hook-shaped cross sections rather than the generally triangular shape shown in FIG. 2. As yet another example, one or more of the teeth 30, 32 can have different cross-sections and/or interruptions.

The jaws 20, 22, 24 and 26 of the bone plate 12 are configured to accommodate a large variety of rib sizes and shapes. With reference to FIG. 3, the jaws 24, 26 decrease in thickness as the jaws 24, 26 extend from the supports 74, 76 toward the tips 94, 96 thereof. The jaws 24, 26 include bases 140, 142 near the supports 74, 76 and thicknesses 144, 146 of the jaws 24, 26 at the bases 140, 142. The thickness of each of the jaws 24, 26 gradually decreases as the jaw 24, 26 extend away from the bases 140, 142. The gradual decrease in thickness of the jaws 24, 26 as the jaws 24, 26 extend away from the bases 140, 142 permits the jaws 24, 26 to clamp both relatively thick and relatively thin cortical bones 36B without exceeding a predetermined amount of the deflection of one or both of the jaws 24, 26 and corresponding stress at the base 140.

More specifically and with reference to FIG. 4, for a thicker cortical bone 36B, teeth 160A-160C of the jaw 26 may engage the interior surface 41 of the cortical bone 36B, teeth 162A-162C of the jaw 24 may engage the exterior surface 43 of the cortical bone 36B, and teeth 162D-162H may be spaced from the exterior surface 43 and not engaged with the cortical bone 36B. The teeth 162D-162H would be spaced from the exterior surface 43 in this example because the thicker cortical bone 36B shifts the base 140 of the jaw 24 away from the jaw 26 due to the engagement of the teeth 162A-162C with the exterior surface. By contrast, for a thinner cortical bone 36B, the teeth 160A-160C of the jaw 26 may engage the interior surface 41 of the cortical bone 36B, the teeth 162A-162C of the jaw 26 may be spaced from the exterior surface 43 of the cortical bone 36A, and the teeth 162D-162H may engage the exterior surface 43 of the cortical bone 36B. Because the cortical bone 36B is thinner, the cortical bone 36B does not shift the base 140 of the jaw 24 away from the jaw 24 but instead shifts the tip 94 due to the engagement of the teeth 162D-162H. The engagement of the jaws 24, 26 with the thinner cortical bone 36B is similar to the configuration shown in FIG. 2, where teeth 32 of the jaw 24 near the base 140 (see FIG. 3) are spaced from the cortical bone 36B whereas the teeth 32 of the jaw 24 near the tip 94 (see FIG. 3) are engaged with the cortical bone 36B. It will be appreciated that the jaws 20, 22 and 22, 24 may thereby clamp and fix the bone plate 12 to cortical bones 36A, 36B having varying thicknesses by engaging the bones 36A, 36B with different sections of the clamping teeth 30, 32 depending on the thickness of the bones 36A, 36B. The decreasing thickness of the jaws 24, 26 provides this flexibility by permitting the teeth 32 near the tips 94, 96 to be spaced from or otherwise not tightly engaged with thicker cortical bone 36B. By contrast, if the jaws 24, 26 have uniform thicknesses along their length, all of the teeth 32 may engage the thicker cortical bone 36B which could require the jaws 24, 26 to be deflected apart farther and could increase the stress at the bases 140, 142 of the jaws 24, 26.

Figure 5:
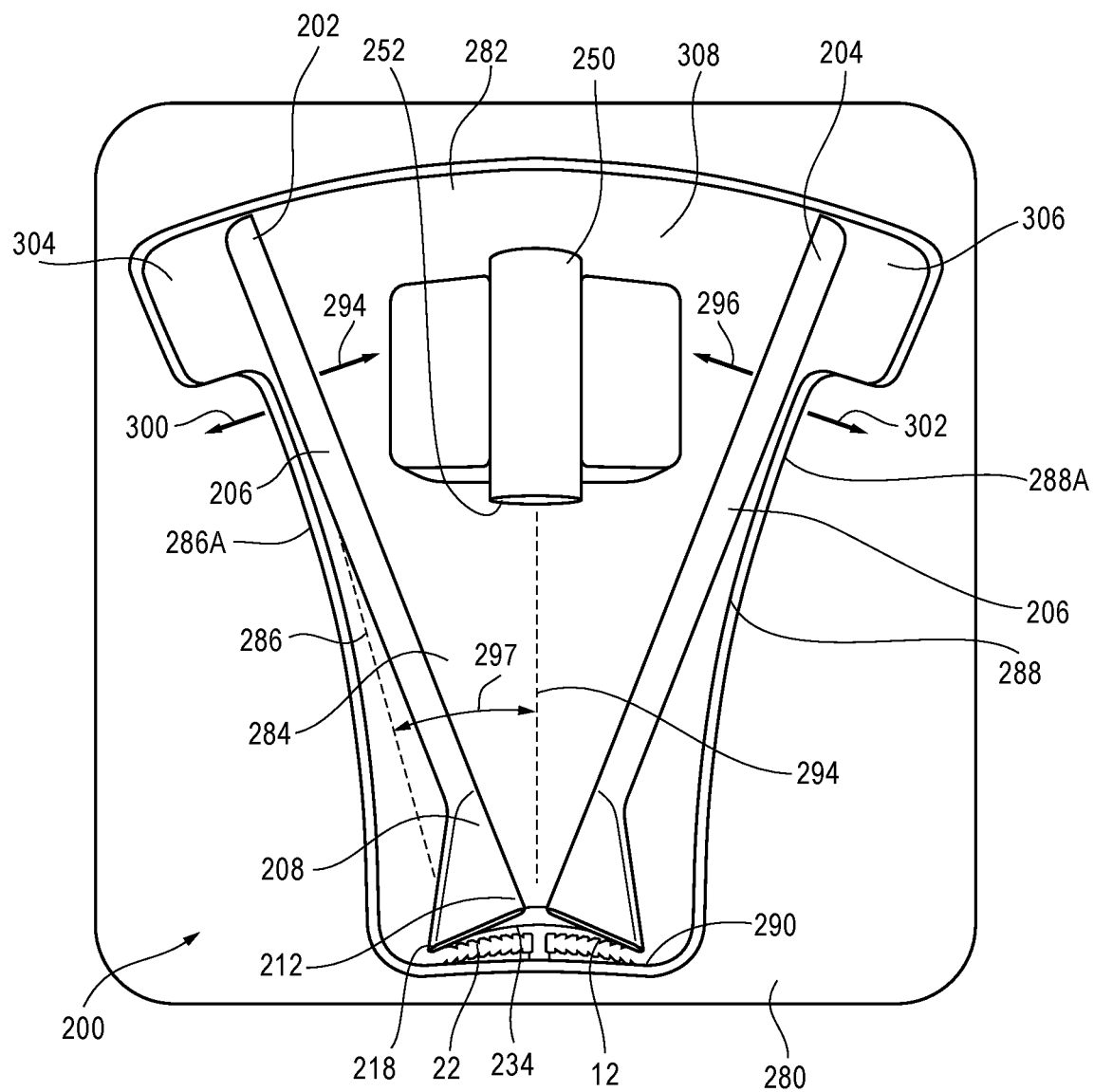
FIG. 5 is a plan view of an inserter tool and the bone plate of FIG. 1 mounted in a tray.
Figure 6:
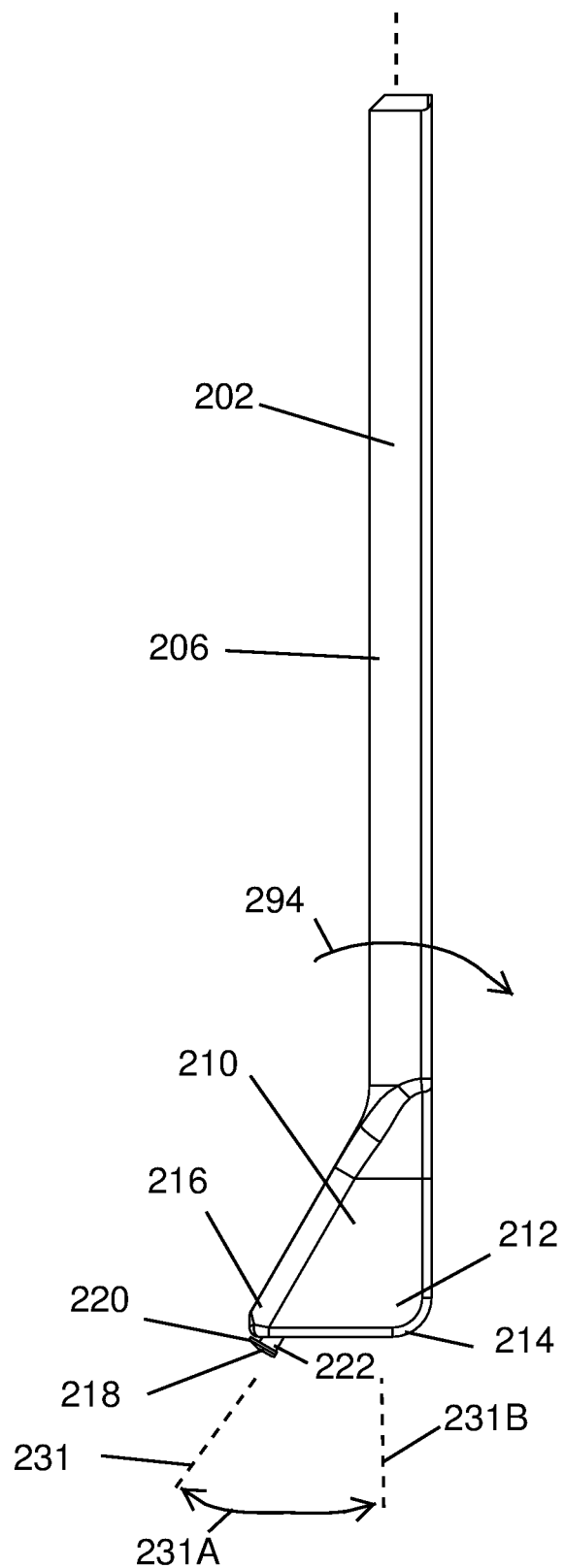
FIG. 6 is a front elevational view of a lever of the inserter tool showing a foot of the tool having a fulcrum at a heel of the foot and a stud at a toe of the foot.
Figure 7:
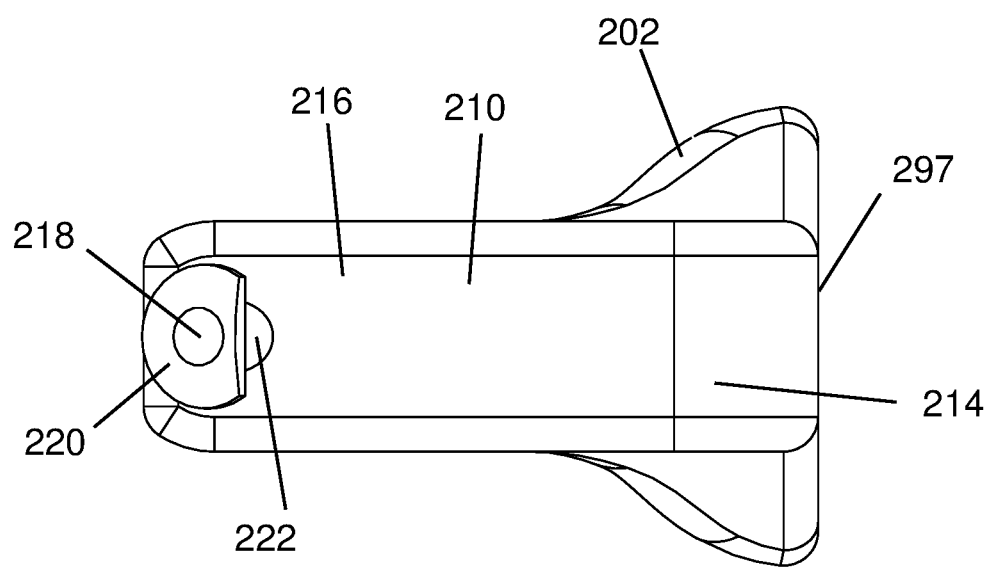
FIG. 7 is a bottom plan view of the lever of FIG. 6 showing a bottom surface of the foot extending between the fulcrum and the stud.

With reference to FIGS. 5 and 6, an inserter tool 200 is shown for holding the bone plate 12 and reconfiguring the jaws 20, 22, 24, 26 to the open configuration by deflecting the jaws 20, 24 away from the jaws 22, 26. The inserter tool 200 includes a pair of levers 202, 204 each having a handle 206 and a plate engaging portion 208. The plate engaging portion 208 includes a foot 210 (see FIG. 6) having a heel 212 with a fulcrum 214 and a toe 216 having a stud 218. The stud 218 has a head 220 and a shaft 222 sized to fit within openings 223 of claw 225, 227 of the upper jaws 20, 24 (see FIGS. 1 and 11). The stud shaft 222 extends along an axis 231 which is oriented at an angle 231A to a longitudinal axis 231B of the lever handle 206.

Figure 8:
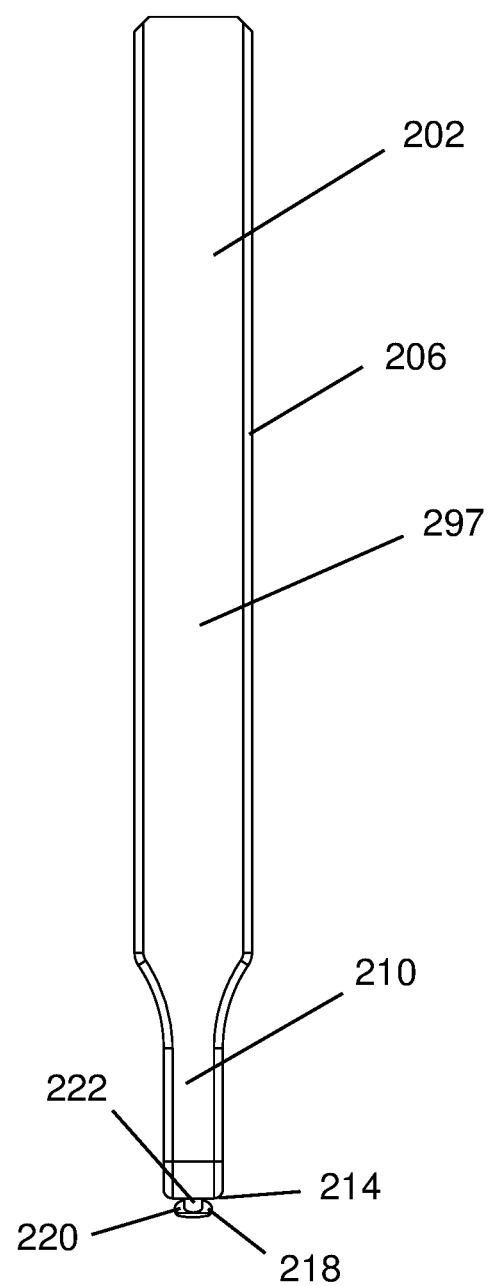
FIG. 8 is a side elevational view of the lever of FIG. 6 showing a surface for abutting the other lever of the inserter tool.
Figure 9:
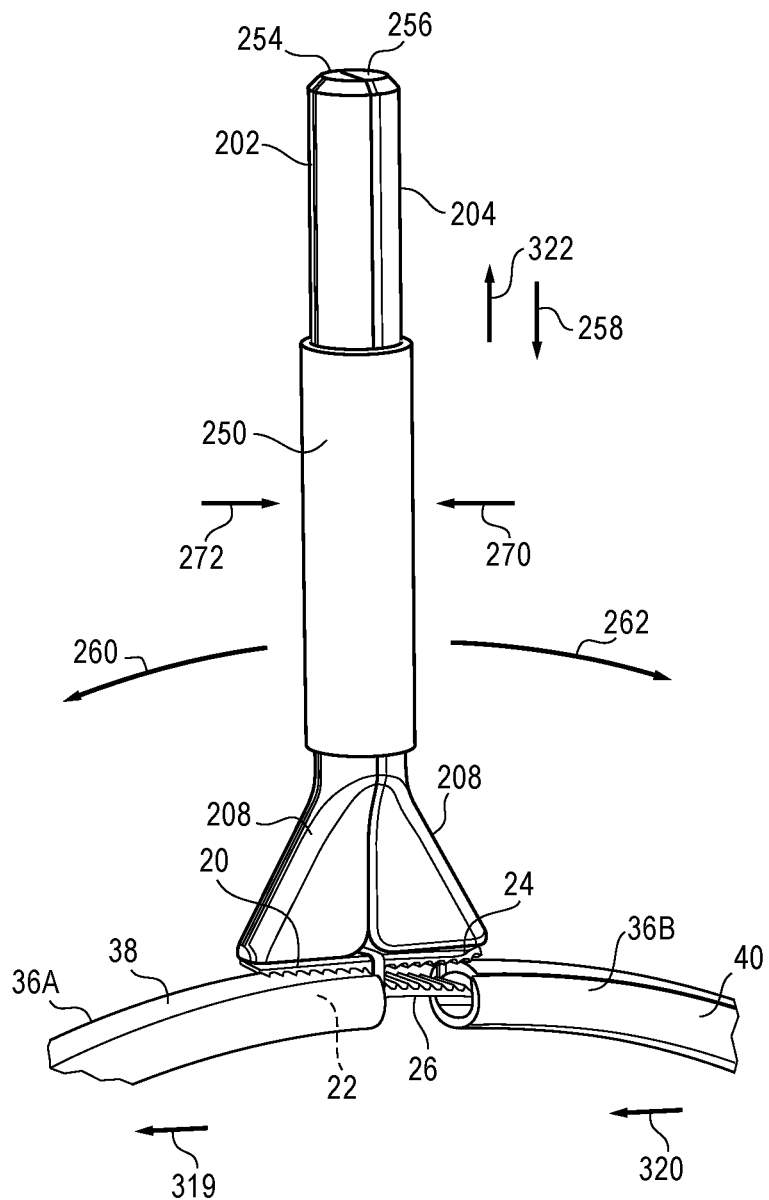
FIG. 9 is a schematic view of the inserter tool of FIG. 5 being used to maintain upper jaws of the bone plate of FIG. 1 in the deflected, open configuration and connect the jaws to cut rib portions.

To connect the lever 202 to the jaw 20, the lever 202 is manipulated to align the stud 218 with the opening 223 of the claw 225. The stud 218 is then moved in direction 230 (see FIG. 11) to advance the stud shaft 222 into the claw opening 223 and engage the stud shaft 222 with a surface 232 extending about the claw opening 223. This positions the stud head 220 below the upper jaw 20. Next, the fulcrum 214 is positioned against a central, upper surface 234 of the jaw 20 near the supports 74, 76 (see FIG. 5). With the stud head 220 engaged with the underside of the jaw 20 and the fulcrum 214 abutting the jaw central, upper surface 234, pivoting the lever 202 in direction 294 (see FIG. 6) causes the stud 218 to pull the upper jaw 20 upward and shift the upper jaw 20 away from the lower jaw 22. In this manner, the levers 202, 204 may each be connected to the respective claws 225, 227 of the jaws 20, 24 (see FIGS. 1 and 11) and pivoted together in directions 294, 296 (see FIG. 5) to substantially simultaneously pull both of the jaws 20, 24 away from the jaws 22, 26 and reconfigure the jaws 20, 22, 24, 26 to the open configuration. As shown in FIGS. 8 and 9, the levers 202, 204 each have a flat surface 297 that abuts the flat surface 297 of the other lever 202, 204 and restricts opening of the jaws 20, 24 beyond a predetermined position.

With respect to FIG. 5, the inserter tool 200 also includes a sleeve 250 for maintaining the levers 202, 204 in the pivoted position where the flat surfaces 297 abut and the jaws 20, 24 have been pulled upward. More specifically, once the levers 202, 204 have been pivoted in directions 294, 296 to open the jaws 20, 24, the sleeve 250 is manipulated to position a throughbore 252 of the sleeve 250 into alignment with ends 254, 256 of the levers 202, 204 (see FIG. 5). With reference to FIG. 9, the sleeve 250 is then advanced in direction 258 over the levers 202, 204 so that the ends 254, 256 extend proximally from the sleeve 250. Due to the resilient properties of the bone plate 12, the jaws 20, 24 are naturally biased toward the jaws 22, 26 in response to using the levers 202, 204 to deflect the upper jaws 20, 24, as discussed above. This biasing force urges the levers 202, 204 engaged with the jaws 20, 24 apart in directions 260, 262, as shown in FIG. 9. The sleeve 250 applies a reactive compressive force in directions 270, 272 inwardly against the levers 202, 204 to resist separation of the levers 202, 204.

With respect to FIG. 5, a tray 280 is shown having a compartment 282 configured to receive the bone plate 12, the levers 202, 204 connected to the bone plate 12, and the sleeve 250. The tray 280 maintains the bone plate 12 and levers 202, 204 in a preassembled configuration and permits rapid, one-handed removal of the bone plate 12 and levers 202, 204 preassembled thereto in an operating room environment, as will be discussed in greater detail below. Further, the tray 280 may be utilized in conjunction with a box, shrinkwrap, or other packaging and permits secure storage and transport of the bone plate 12 and inserter tool 200.

The compartment 282 includes a recess 284 and side walls 286, 288 extending therealong that generally bow outwardly away from a sidewall 290 that supports the bone plate 12, as shown in FIG. 5. The sidewalls 286, 288 are arranged to extend at an angle 297 relative to a center line 294 of the tray 280 and support the handles 206 in a partially pivoted position (which produces a partial deflection of the jaws 20, 24 away from the jaws 22, 26). More specifically, to insert the levers 202, 204 and the bone plate 12 into the tray 280, the levers 202, 204 are first connected to the bone plate 12 using the studs 218 and bone plate claws 225, 227 as discussed above. Next, the levers 202, 204 are pivoted toward each other in directions 294, 296 (see FIG. 5), which deflects the jaws 20, 24 away from the jaws 22, 26, and the connected levers 202, 204 and bone plate 12 are inserted into the compartment 282. The handles 206 of the levers 202, 204 are released and the resilient properties of the bone plate 12 biases the deflected jaws 20, 24 back toward the jaws 22, 26 which in turn biases the levers 202, 204 apart in directions 300, 302 as shown in FIG. 5. The tray sidewalls 286, 288 resist the bias force applied in directions 300, 302 from the levers 202, 204. The bias force of the levers 202, 204 outwardly in directions 300, 302 creates a preload on the assembly of the levers 202, 204 and the bone plate 12 in the tray compartment 282 which firmly engages the levers 202, 204 and bone plate 12 connected thereto within the compartment 282 of the tray 280.

The tray 280 may also have portions 304, 306 of the recess 284 at proximal ends of the levers 202, 204 in order to permit a user to withdraw the levers 202, 204 and connected bone plate 12 from the tray 280 in a one-handed operation. For example, a user may insert the thumb of his right hand into recess portion 304, wrap his thumb around the handle 206 of the lever 202, insert the index and middle finger of his right hand into the recess portion 306, wrap his index and middle fingers around the handle 206 of the lever 204, and then make a first with his right hand. This motion moves the handles 206 outward from beneath overhangs 286A, 288A of the sidewalls 286, 288, pivots the levers 202, 204 toward each other in directions 294, 296, and shifts the jaws 20, 24 away from the jaws 22, 26. The levers 202, 204 and bone plate 12 are connected thereto (with jaws 20, 22, 24, 26 in the open configuration) may then be withdrawn from the tray 280.

The compartment 282 may further include a recess 308 below the sleeve 250 that permits the user to withdraw the sleeve 250 with one hand after removing the levers 202, 204 and connected bone plate 12 with the other hand. Continuing with the example above, after the user has withdrawn the levers 202, 204 and connected bone plate 12 with his right hand, the user can insert the thumb of his left hand into the recess 308 on one side of the sleeve 250, insert the index through pinky fingers of his left hand into the recess 308 on the other side of the sleeve 250, grasp the sleeve 250 with his left hand, then remove the sleeve 250 from the tray 280.

In this manner, the user may insert a first hand into the compartment 282 and grasp the handles 206 of the levers 202, 204, compress the handles 206 toward one another, withdraw the assembled levers 202, 204 and bone plate 12 from the compartment 282 with the first hand, and then insert his other hand into the compartment 282 and remove the sleeve 250 in one fluid movement for each hand. After removing the levers 202, 204, bone plate 12, and sleeve 250 from the tray 280, the user may then pivot the levers 202, 204 into the abutting configuration of FIG. 9 and then slide the sleeve 250 downward over the lever ends 254, 256 in direction 258 (see FIG. 9). The sleeve 250 maintains the levers 202, 204 in the abutting orientation, keeps the levers 202, 204 connected to the jaws 20, 22, and maintains the jaws 20, 22, 24, 26 in the open configuration. In this manner, the sleeve 250, levers 202, 204, and bone plate 12 are easy to assemble and handle within the operating room.

With reference to FIG. 9, the inserter tool 200 may be used to position the bone plate 12 on the rib sections 38, 40. More specifically, with the sleeve 250 maintaining the levers 202, 204 in the abutting configuration, the jaw 20 is maintained deflected away from the lower jaw 22 which permits the jaws 20, 22 to be advanced in direction 319 so that the cortical bone 36A advances into the gap 50 between the jaws 20, 22 (this operation is similar to the movement of the jaws 24, 26 discussed above with respect to FIG. 4A). The sleeve 250 maintaining the levers 202, 204 in the abutting configuration also maintains the jaw 24 deflected away from the jaw 26. This permits the rib cortical bone 36B to be advanced in direction 320 into the bone receiving gap 52 between the jaws 24, 26 (this operation is similar to the movement of the jaws 20, 22 discussed above with respect to FIG. 4B).

With the cortical bones 36A, 36B in the desired positions between the jaws 20, 22 and 24, 26, the sleeve 250 is then slid off of the levers 202, 204 in direction 322, as shown in FIG. 9. This permits the levers 202, 204 to pivot away from one another in directions 260, 262. The resilient properties of the bone plate 12 bias the upper jaws 20, 24 back toward the lower jaws 22, 26 and reconfigure the jaws 20, 22, 24, 26 to the clamping configuration. The jaws 20, 22, 24, 26 clamp the cortical bones 36A, 36B therebetween and fix the bone plate 12 to the rib sections 38, 40. The levers 202, 204 may then be disconnected from the bone plate 12 by moving the studs 218 in directions 322, 324 (see FIG. 11) out of engagement with the claws 225, 227 of the bone plate upper jaws 20, 24.

The bone plate 12 may be made of a variety of different materials. In one approach, the bone plate 12 is made of super elastic nitinol that resiliently permits deflection of one or both of the jaws 20, 22 and 24, 26 to reconfigure the jaws 20, 22, 24, 26 to the open configuration. In another approach, the bone plate 12 may be made of a shape-memory Nitinol where the jaws 20, 22, 24, 26 shift to an open configuration when the bone plate 12 is chilled, such as by submerging the bone plate 12 in saline, to a temperature below the internal temperature of the patient. With the bone plate 12 chilled and the jaws 20, 22, 24, 26 in the open configuration, the jaws 20, 22, 24, 26 may not be biased toward each other (due to the crystalline structure of the chilled nitinol bone plate 12). However, positioning the bone plate 12 on the rib sections 38, 40 within the patient raises the temperature of the bone plate 12 and reconfigures the jaws 20, 22, 24, 26 to a clamping configuration. With the bone plate 12 at this elevated temperature, the shape-memory properties of the Nitinol bias one or more of the jaws 20, 22 and 24, 26 together and causes the jaws 20, 22, 24, 26 to clamp the cortical bones 36A, 36B. In other approaches, the bone plate 12 may be made of polyether ether ketone (PEEK), titanium, or other biocompatible plastics, metals, or alloys.

Figure 13:
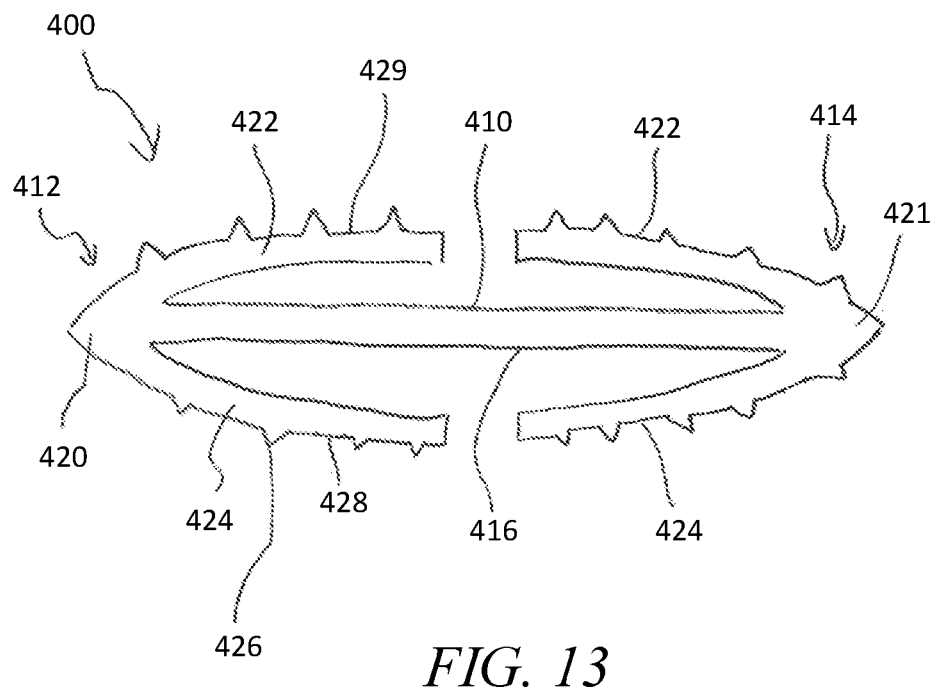
FIG. 13 is a front elevational view of another bone plate system showing a bone plate having arms in an initial, undeflected configuration.
Figure 14:
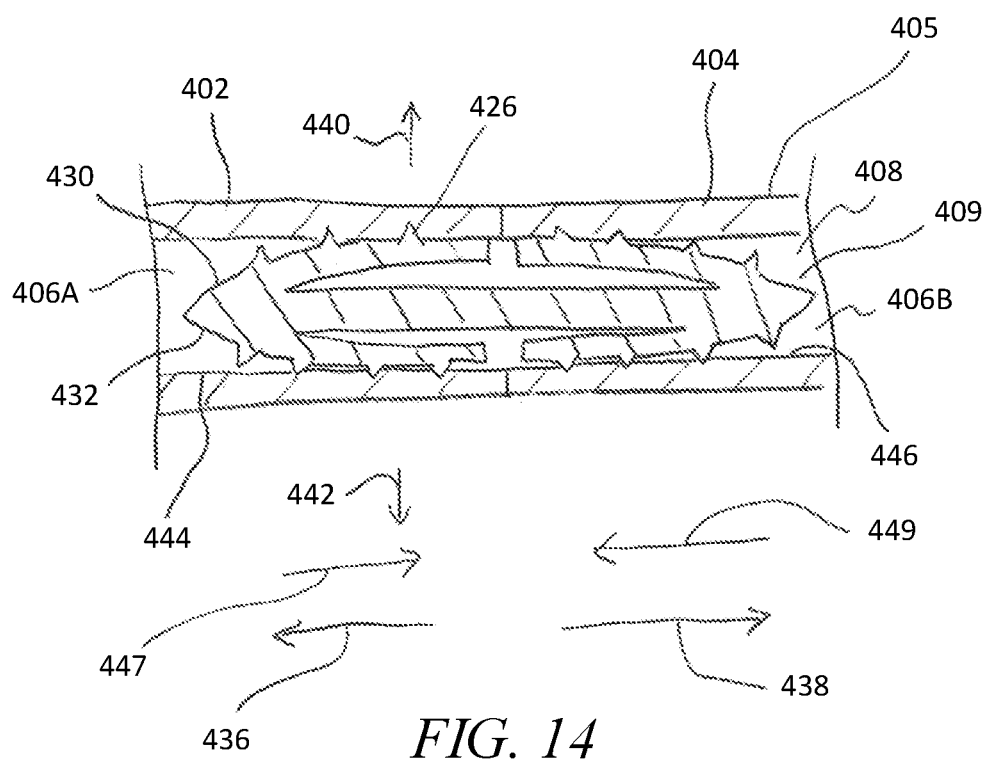
FIG. 14 is a cross-sectional view of the bone plate of FIG. 13 showing the bone plate received within the intramedullary canal of a cut rib.

With reference to FIGS. 13 and 14, another bone plate system 400 is shown for securing bones such as sections 402, 404 of a broken rib 405. The bone plate system 400 is similar in many respects to the bone plate system 10 discussed above such that differences between the two will be highlighted. One difference is that the bone plate system 400 is configured to fit entirely with sections 406, 408 of an intramedullary canal 409 of the rib 405, whereas the jaws 20, 24 of the bone plate 12 are disposed outside of the rib 39. More specifically, the bone plate system 400 includes a bone plate 410 having anchor devices 412, 414 for fixing the bone plate 410 to the rib sections 402, 404. The bone plate 410 has a body 416 connecting the anchor devices 412, 414 and opposite leading ends 420, 421 configured to be advanced into the intramedullary canal sections 406, 408. The anchor devices 412, 414 each include a pair of resilient arms 422, 424 extending away from the leading ends 420, 421. The arms 422, 424 have teeth 426 along outer surfaces 428, 429 of the arms 422, 424. The bone plate 410 may be made of a resilient material, such as super elastic ninitol, such that the arms 422, 424 are biased outwardly into an expanded configuration as shown in FIG. 13.

The leading ends 420, 421 include inclined surfaces 430, 432 configured to cam against internal surfaces 444, 446 of the intramedullary canal sections 406, 408 and deflect the arms 422, 424 inward. In use, the leading end 420 is advanced into the intramedullary canal section 406 in direction 436 and the leading end 421 is advanced in direction 438 into the intramedullary canal 408. Inserting the ends 420, 421 into the canal sections 406, 408 deflects the arms 422, 424 toward one another due to the camming engagement of the surfaces 430, 432 against the internal surfaces 444, 446 of the intramedullary canal sections 406, 408. The rib sections 402, 404 are brought together in directions 447, 449 to fully advance the bone plate leading ends 420, 421 into the intramedullary canal sections 406, 408. The resilient properties of the bone plate 410 bias the deflected arms 422, 424 apart in directions 440, 442 which drives the teeth 426 of the arms 422, 424 into the interior surfaces 444 and 446 of the intramedullary canal sections 406, 408. In this manner, the bone plate 410 is fixed to the rib sections 402, 404 while being disposed entirely within the rib sections 402, 404.

Figure 15:
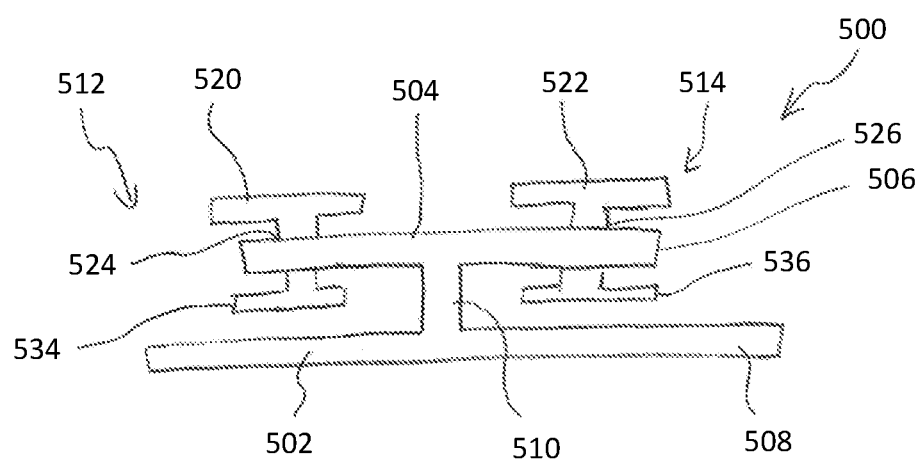
FIG. 15 is a front elevational view of another bone plate system having a bone plate and clamp screws carried on the bone plate.
Figure 16:
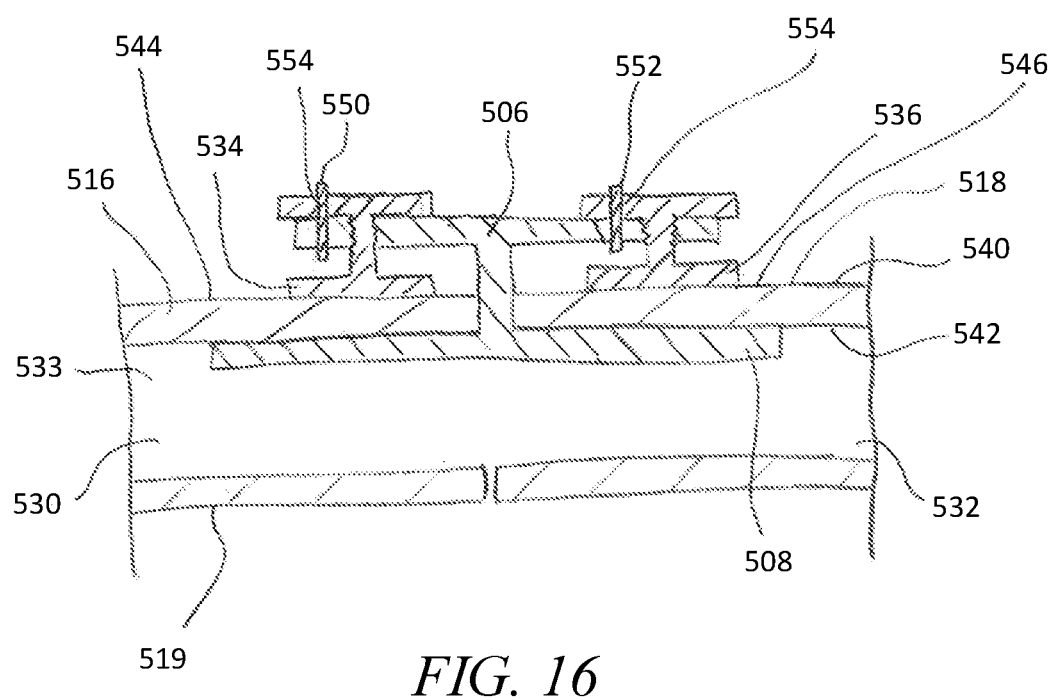
FIG. 16 is a cross-sectional view of the bone plate system of FIG. 15 showing the bone plate system stabilizing a cut rib.

With reference to FIGS. 15 and 16, another bone plate system 500 is provided that is similar in many respects to the bone plate systems 10, 400 discussed above such that differences between the bone plate system 500 and bone plate systems 10, 400 will be highlighted. One difference is that the bone plate system 500 includes a bone plate 502 having a body 504 with an upper portion 506 and a lower portion 508 connected by a support 510. The bone plate 502 has anchor devices 512, 514 for fixing the bone plate 502 to sections 516, 518 of a cut rib 519. The anchor devices 512, 514 include clamp screws 520, 522 engaged with threaded openings 524, 526 of the upper portion 506.

With reference to FIG. 16, the bone plate 502 is connected to the rib sections 516, 518 by inserting the bone plate lower portion 508 into sections 530, 532 of an intramedullary canal 533 of the rib 519. The clamp screws 520, 522 may be shifted to a clamping configuration which shifts engaging members 534, 536 of the clamp screws 520, 522 against an external surface 540 of the rib sections 516, 518. Shifting the clamp screws 520, 522 to the locked position draws the bone plate lower portion 508 against an interior surface 542 of the ribs 516, 518. Continued shifting of the clamp screws 520, 522 toward the locked position thereof tightly clamps cortical bones 544, 546 of the rib sections 516, 518 between the engaging members 534, 536 and the plate lower portion 508. The anchor devices 512, 514 may further include a lock device, such as a pins 550, 552 inserted into openings 554 in the clamp screws 520, 522 and the plate upper portion 506 after the clamp screws 520, 522 have been driven to the locked position. The pins 550, 552 restrict movement of the clamp screws 520, 522 away from the locked positions thereof and corresponding disengagement of the clamp members 534, 536 from the cortical bones 544, 546.

Figure 17:
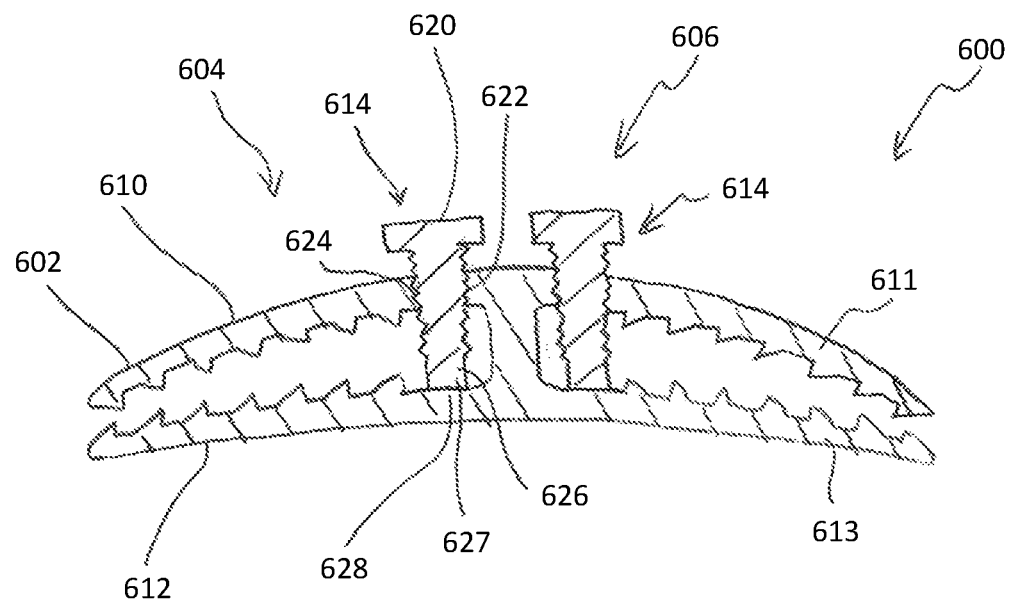
FIG. 17 is a cross-sectional view of another bone plate system including a bone plate having a pair of bolts for adjusting the position of jaws of the bone plate.
Figure 18:
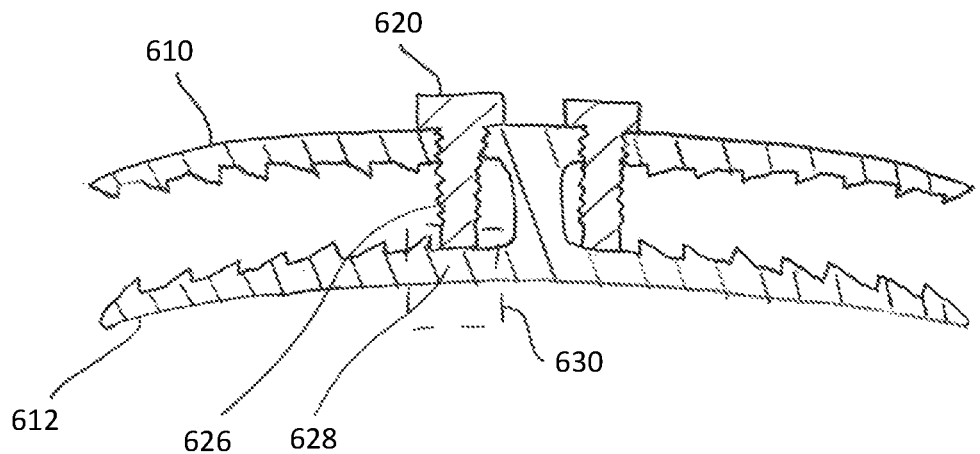
FIG. 18 is a cross-sectional view similar to FIG. 17 showing the jaws of the bone plate shifted to an open configuration.

With reference to FIGS. 17 and 18, a bone plate system 600 is shown that is similar in many respects to the bone plate system 10 discussed above such that differences between the two will be highlighted. One difference is that the bone plate system 600 includes a bone plate 602 having anchor devices 604, 606 for fixing the bone plate 602 to bone portions. The anchor devices 604, 606 include jaws 610, 612 and 611, 613 and expansion devices 614 for shifting the jaws 602, 604 between clamping and open configurations. With reference to jaws 610, 612, the device 614 includes a bolt 620 having a threaded shank 626 engaged with threads 622 of an opening 624 in the upper jaw 610. The bolt shank 626 has a distal end 627 that engages a seat 628 of the lower jaw 612. Turning the bolt 620 in a tightening direction engages the shank distal end 627 against the seat 628. The jaw 612 is configured to be more rigid than the jaw 610 such that continued turning of the bolt 620 threadingly advances the jaw 610 away from the jaw 612 until the jaws 610, 612 reach an open configuration, as shown in FIG. 18.

With the jaws 610, 612 in the open configuration, the jaws 610, 612 may be advanced into position on bone portions, such as cortical bones 36A, 36B (see FIG. 2). Then, the bolt 620 may be turned in a loosening direction that permits the jaw 610 to return to the clamping configuration of FIG. 17 due to the resilient properties of the bone plate 602. In another approach, the bone plate 602 is generally rigid. Rather than rely upon the resilient properties of the bone plate 602 to return the jaw 610 to the clamping configuration, the shank distal end 627 is rotatably connected to the jaw 612, such as by a yoke 630. Turning the bolt 620 in the loosening direction thereby creates tension in the bolt 620 that draws the jaw 610 toward the jaw 612 and reconfigures the jaws 610, 612 to the clamping configuration.

Figure 19:
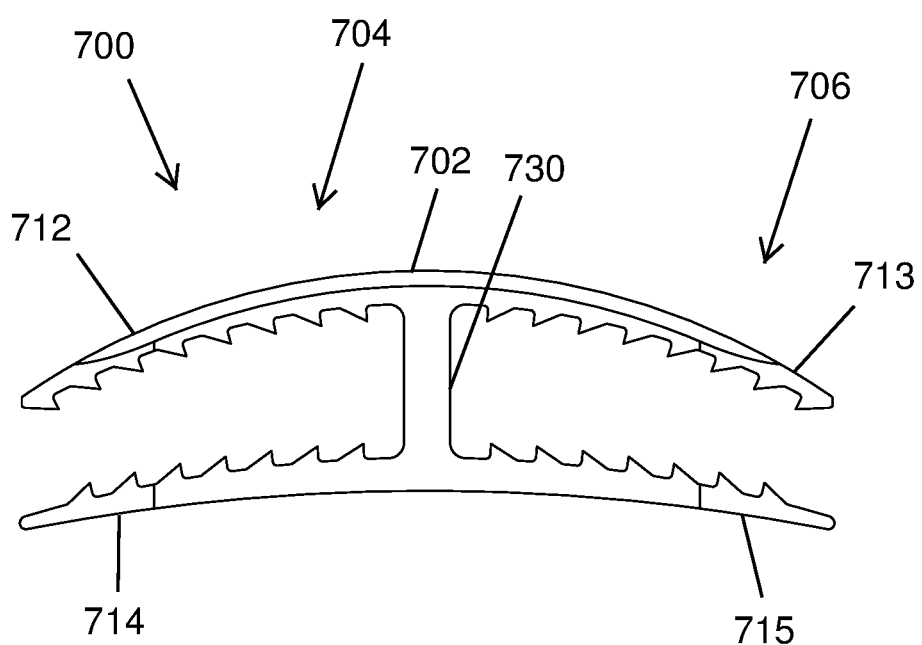
FIG. 19 is a front elevational view of another bone plate system including a bone plate having a support sized to position jaws of the bone plate on anterior and posterior exterior surfaces of a cut rib.
Figure 19A:
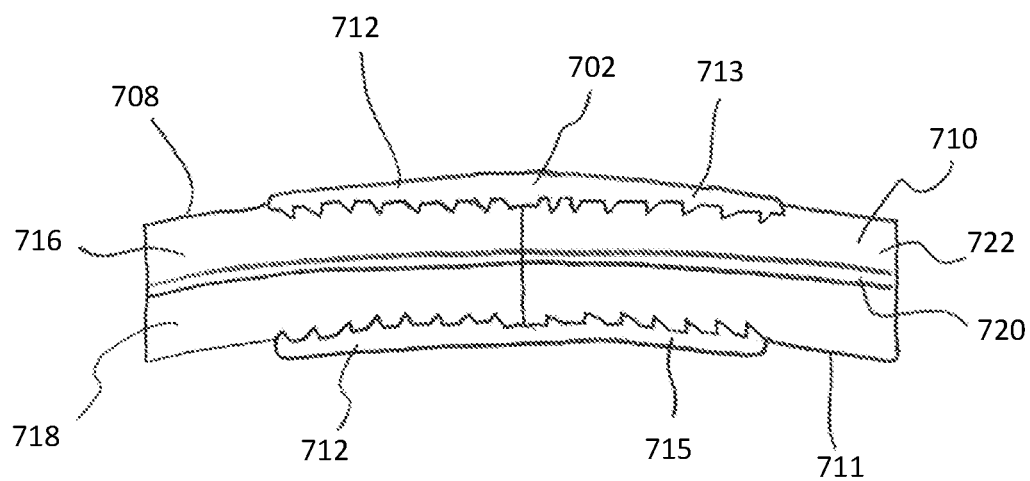
FIG. 19A is a bottom plan view of the bone plate system of FIG. 19 showing the bone plate stabilizing a cut rib and the jaws of the bone plate spaced from a neurovascular bundle running along an underside of the rib.
Figure 20:
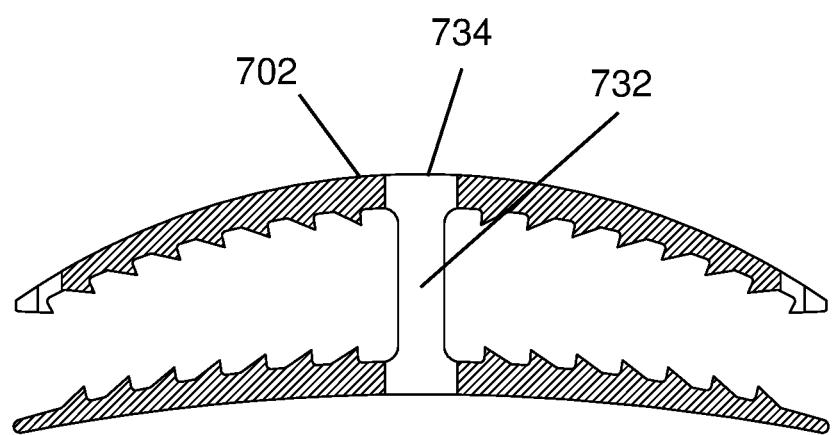
FIG. 20 is a cross-sectional view of the bone plate of FIG. 19 showing a central bone growth window of the bone plate.

With reference to FIGS. 19 and 20, another bone plate system 700 is shown that is similar in many respects to the bone plate system 10 discussed above such that difference between the bone plate systems 10, 700 will be highlighted. One difference between the bone plate systems 10, 700 is that the bone plate system 700 includes a bone plate 702 having anchor devices 704, 706 configured to grip only outer surfaces of sections 708, 710 of a rib 711 (see FIG. 19A) rather than the rib interior surfaces 41, 55 and exterior surfaces 43, 57 as in the bone plate system 10 (see FIG. 2).

More specifically, the anchor devices 704, 706 include front jaws 712, 713 and rear jaws 714, 715 configured to engage, respectively, the anterior and posterior regions 716, 718 of the rib sections 708, 710 as shown in the bottom plan view of FIG. 19A. In this approach, the jaws 712, 713, 714, and 715 are positioned away from a neurovascular bundle 720 running along an underside 722 of the rib section 708, 710.

With reference to FIGS. 19 and 20, the bone plate 702 includes supports 730, 732 sized to extend across the intramedullary canals of the rib sections 708, 710. Further, the bone plate 702 has a bone growth window 734 that permits cortical bone to grow between the rib sections 708, 710.

Figure 21:
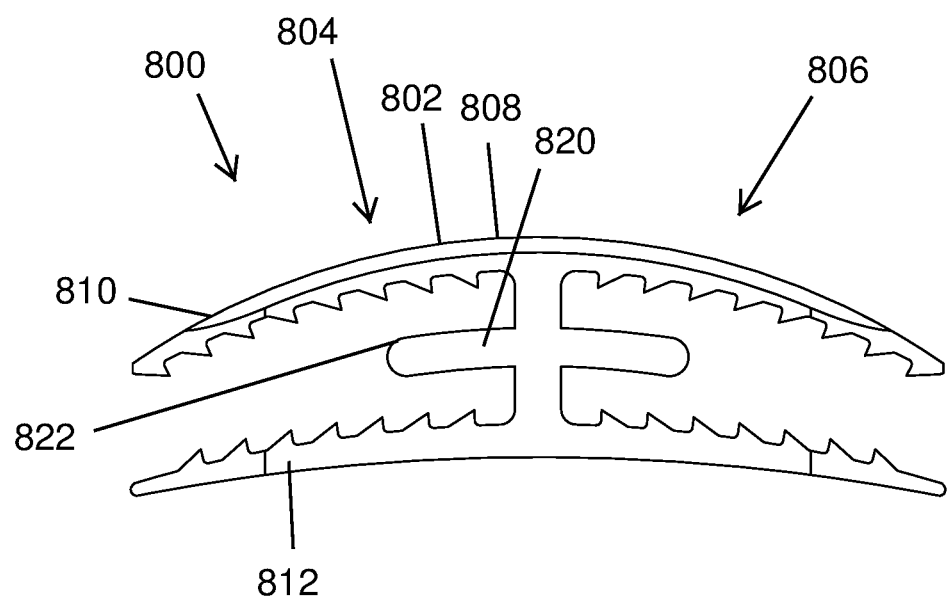
FIG. 21 is a front elevational view of another bone plate system including a bone plate having jaws configured to engage anterior and posterior exterior surfaces of a cut rib and an intramedullary canal brace extending outwardly between the jaws.
Figure 22:
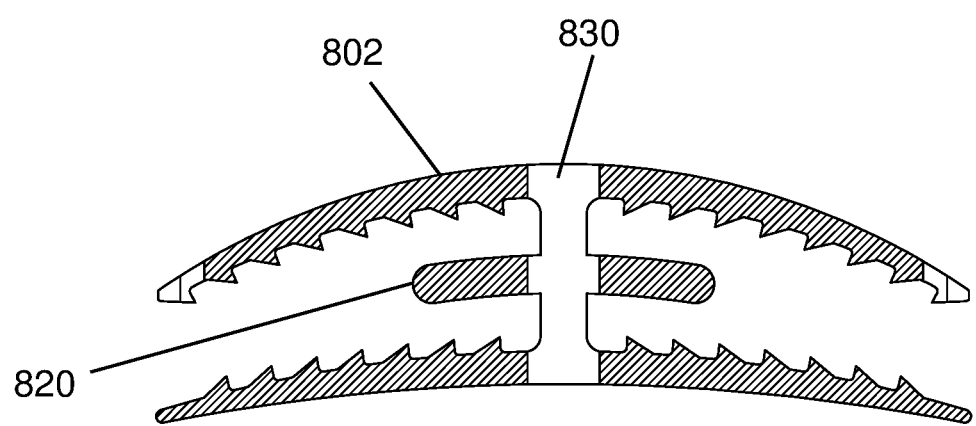
FIG. 22 is a cross-sectional view of the bone plate system of FIG. 21 showing a bone growth window of the bone plate extending through the bone plate.

With reference to FIGS. 21 and 22, another bone plate system 800 is shown that is substantially similar to the bone plate system 700 discussed above. One difference is that the bone plate system 800 includes a bone plate 802 having anchor devices 804, 806 and a body 808 connecting the anchor devices 804, 806. In one form, the anchor devices 804, 806 include jaws 810, 812 for engaging outer surfaces of the rib sections 708, 710 in a manner similar to the jaws 712, 714, However, the anchor devices 804, 806 further include a brace 820 configured to extend into and along the intramedullary canals of the rib sections 708, 710. The brace 820 may have an outer surface 822 configured to engage interior surfaces of the intramedullary canals of the ribs 708, 710 and provide an additional anchor point for each of the anchor devices 804, 806. In this manner, the anchor devices 804, 806 may engage outer surfaces of the anterior and posterior regions 716, 718 of the rib sections 708, 710 (see FIG. 19A) via the jaws 810, 812 as well as interior surfaces of the intramedullary canals of the rib sections 708, 710 via the brace 820.

With reference to FIG. 22, the bone plate 802 includes a bone growth window 830 extending through the bone plate 802 and between the guides 820 of the anchor devices 804, 806. The bone growth window 830 permits cortical bone growth across the bone plate 802 despite the engagement of the brace 820 with the inner surfaces of the intramedullary canal of the ribs 708, 710.

Figure 23:
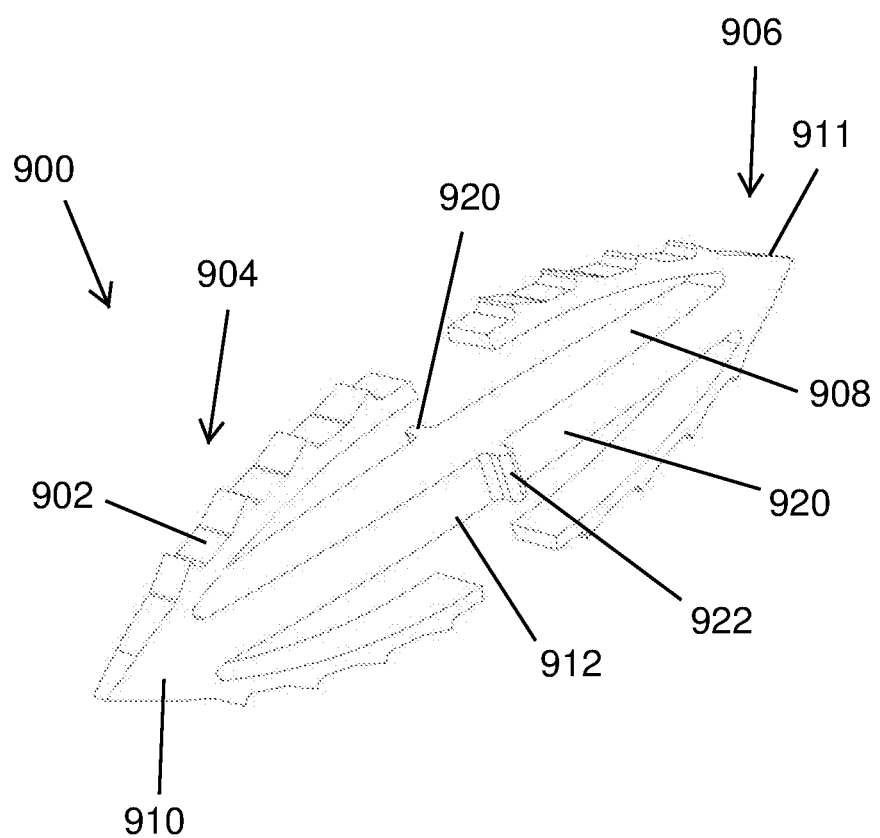
FIG. 23 is a perspective view of another bone plate system including a bone plate with resilient arms.
Figure 24:
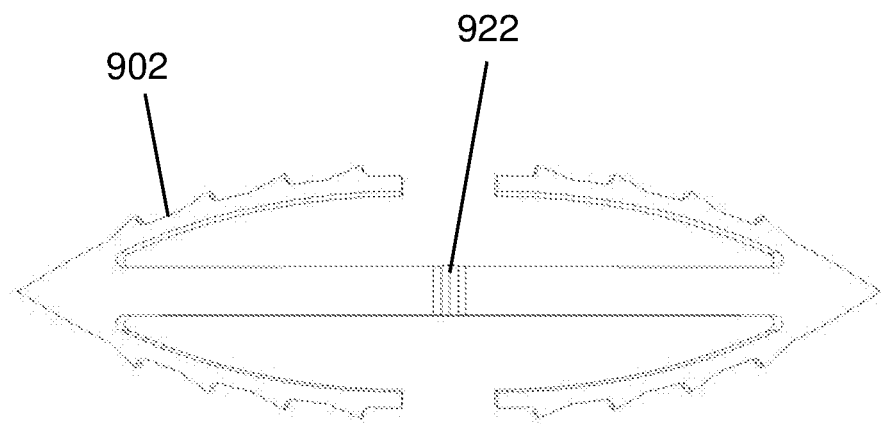
FIG. 24 is a front elevational view of the bone plate system of FIG. 23 showing teeth of the bone plate configured to resist removal of the bone plate from the intramedullary canal of a cut rib.
Figure 25:
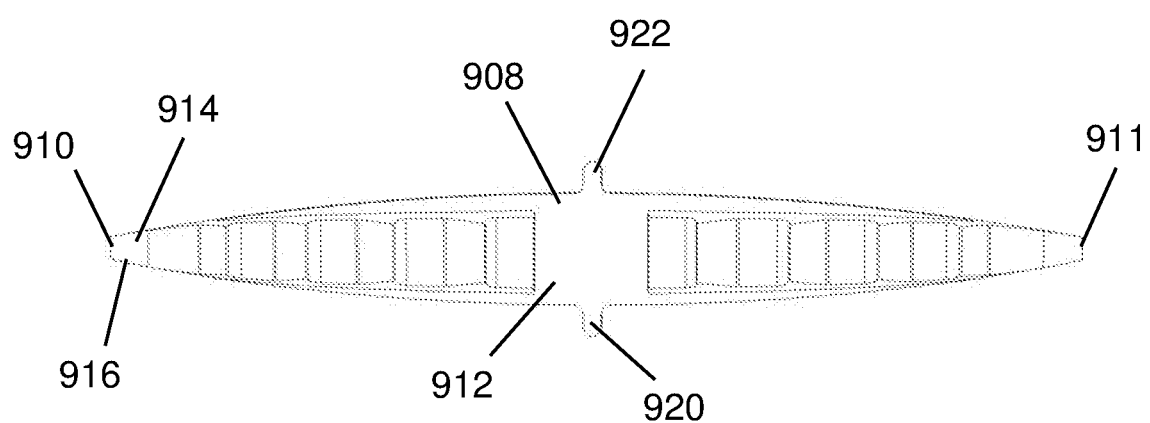
FIG. 25 is a top plan view of the bone plate system of FIG. 23 showing an enlarged, central portion of the bone plate and narrow leading end portions of the bone plate.
Figure 26:
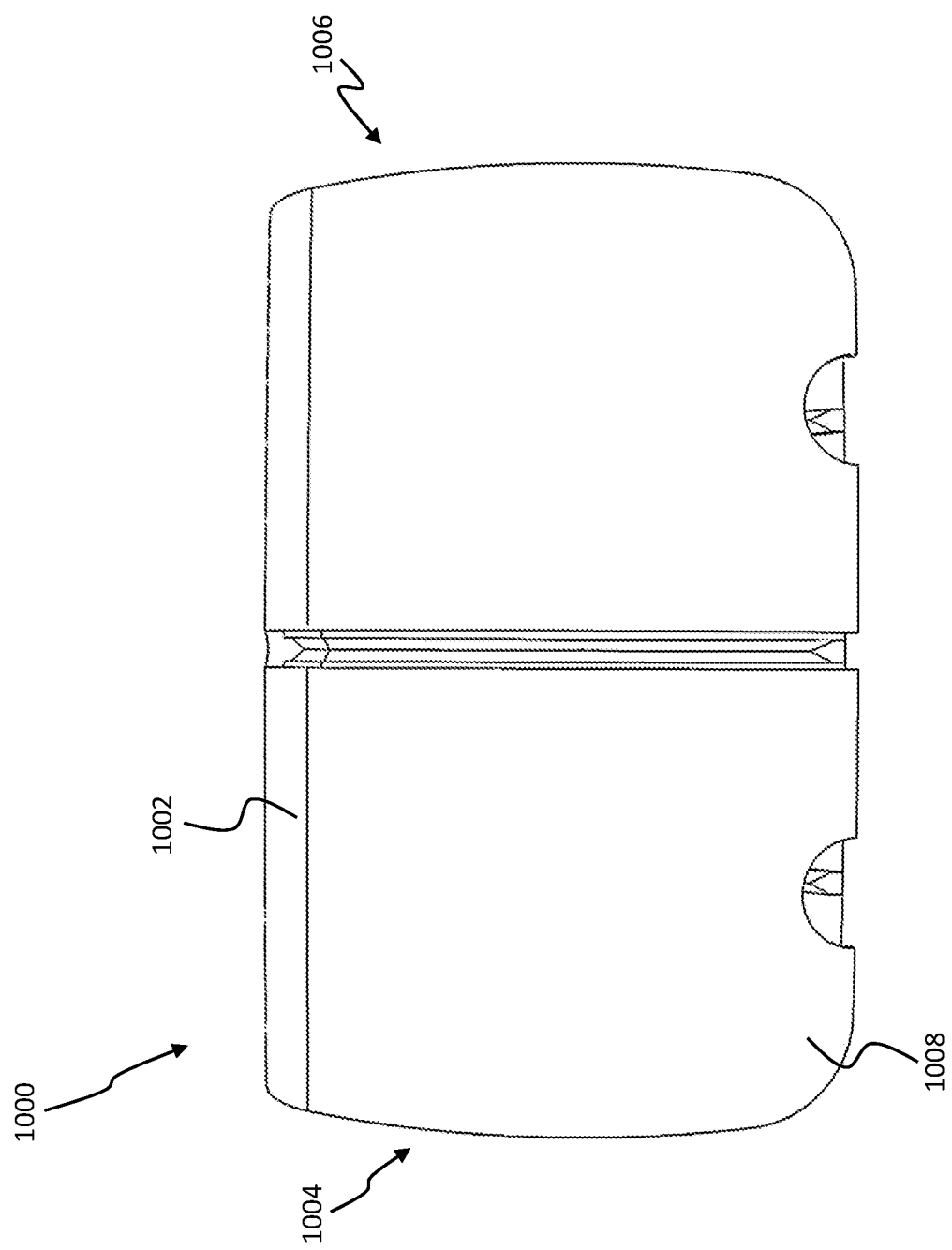
FIG. 26 is a front elevational view of another bone plate system having a bone plate configured to engage anterior and posterior exterior surfaces of a rib.

With reference to FIGS. 23-25, another bone plate system 900 is shown. The bone plate 900 is similar in many respects to the bone plate system 400 discussed above such that the differences between the two will be highlighted. One difference is that the bone plate system 900 includes a bone plate 902 having anchor devices 904, 906 and a body 908 connecting the anchor devices 904, 906. The bone plate 902 has a pair of narrowed leading ends 910, 911 that are narrower relative to a wider central portion 912 of the body 908 (see FIG. 25). With reference to FIG. 25, the leading ends 910, 911 include tapered outer surfaces 914, 916 which converge and provide the narrow profile of the leading ends 910, 911. The narrower leading ends 910, 911 function as wedge to separate and move the cancellous bone within the intramedullary canals 406A, 406B of the rib sections 402, 404.

Another difference between the bone plate 902 and the bone plate 402 is that the bone plate 902 includes barbs 920, 922 at the wider center portion 912. The barbs 920, 922 are configured to engage the cortical bone of the rib sections 402, 404 and prevent the bone plate 902 from being advanced beyond a predetermined position in the intramedullary canals 406A, 406B.

With reference to FIGS. 26-29, another bone plate system 1000 is shown. The bone plate system 1000 includes a bone plate 1002 having a pair of anchor devices 1004, 1006 configured to fix the bone plate 1002 to cut rib sections. Like the bone plate 702, the bone plate 1002 is configured to engage outer surfaces of rib sections 1024, 1026 (see FIG. 28) without contacting a neurovascular bundle running along the underside of the rib sections 1024, 1026. However, the bone plate 1002 is disposed entirely around the rib sections 1024, 1026 rather than extending across the intramedullary canal (the support 730 of the bone plate 702 extends across the intramedullary canals of rib sections 708, 710).

Figure 27:
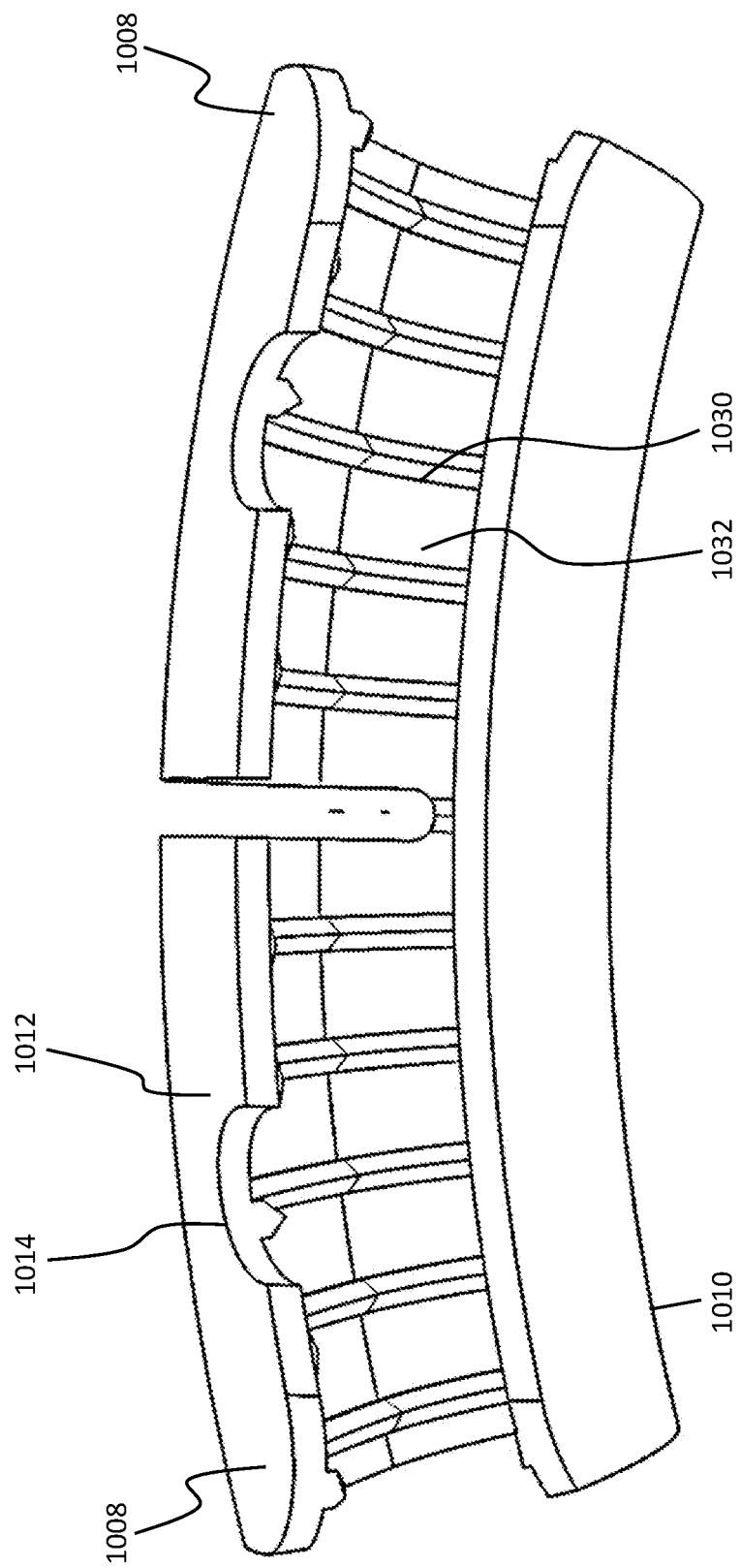
FIG. 27 is a bottom plan view of the bone plate of FIG. 26 showing jaws of the bone plate.

With reference to FIG. 27, the anchor devices 1004, 1006 each include an upper jaw 1008 and a lower jaw 1010 common to both anchor devices 1004, 1006. The upper jaws 1008 each include a claw 1012 with a corresponding opening 1014 for engaging a tool which may be used to pry apart the jaws 1008, 1010 in a manner similar to the inserter tool 200 and bone plate 12 discussed above.

Figure 28:
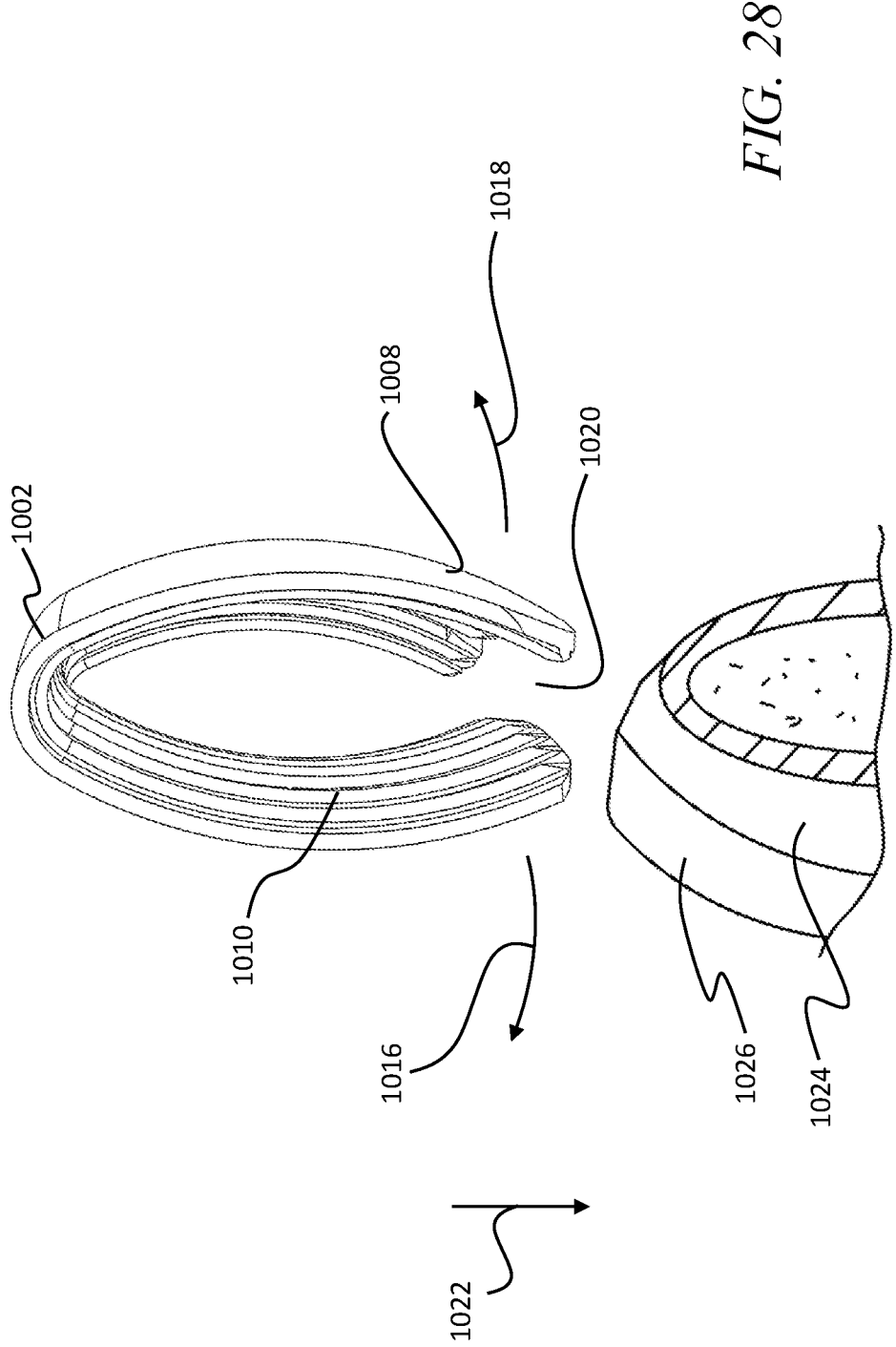
FIG. 28 is a side elevational view of the bone plate of FIG. 26 showing the bone plate being positioned onto a cut rib.

With reference to FIG. 28, the jaws 1008, 1010 have a bone-receiving gap 1020 therebetween. In use, one or both of the jaws 1008, 1010 is shifted outward in directions 1016, 1018 to shift the jaws 1008, 1010 to an open configuration. Next, the bone plate 1002 is advanced downward in direction 1022 onto the rib sections 1024, 1026 and the one or both jaws 1008, 1010 are released. The resilient properties of the bone plate 1002 bias the jaws 1008, 1010 together which clamps the jaws 1008, 1010 against the rib sections 1024, 1026. With reference to FIG. 27, the bone plate 1002 includes raised, pointed beads 1030 extending along an interior surface 1032 of the bone plate 1002. The pointed beads 1030 bite into the outer surfaces of the ribs 1024, 1026 and restrict movement of the bone plate 1002 relative to the rib sections 1024, 1026.

Figure 29:
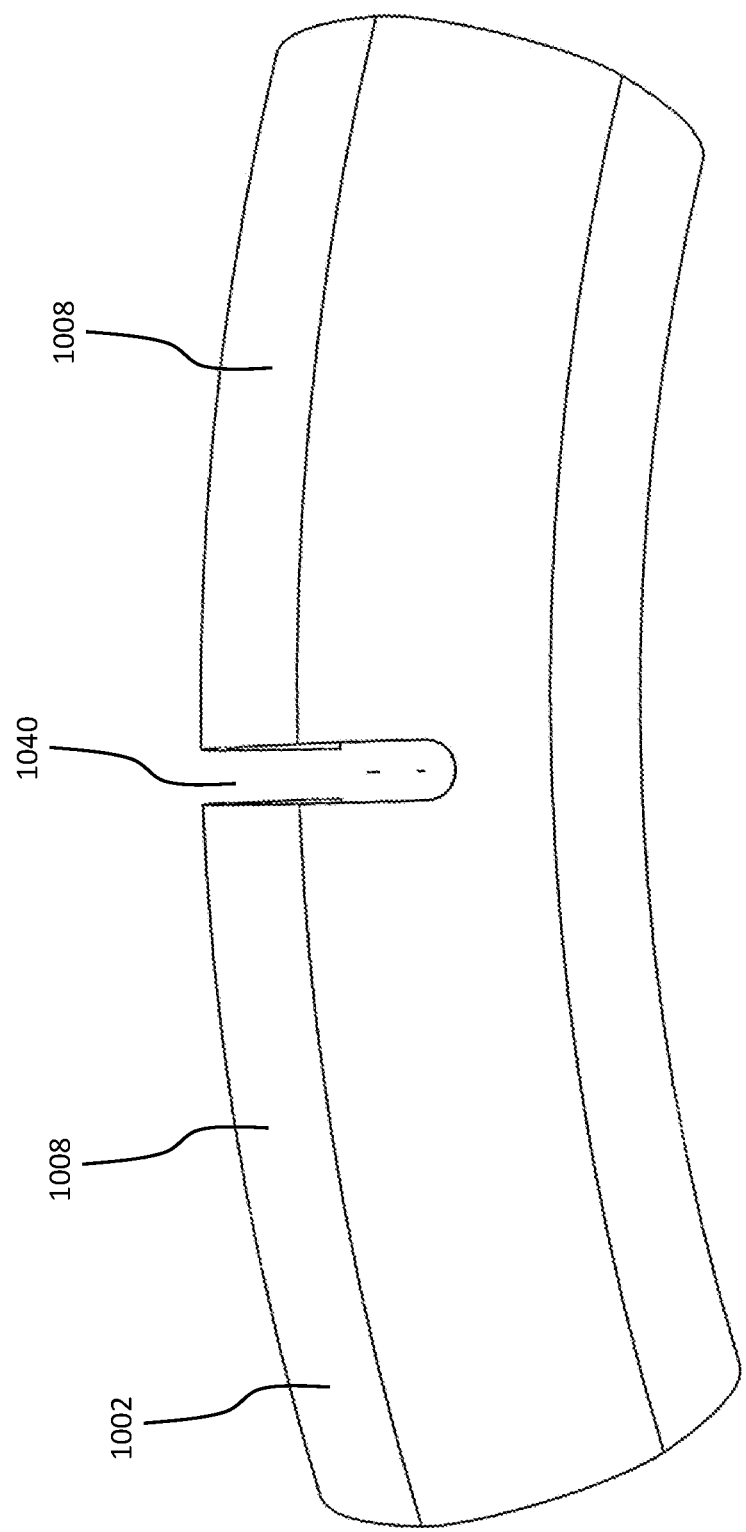
FIG. 29 is a top plan view of the bone plate of FIG. 26 showing a cutout between upper jaws of the bone plate.

With reference to FIG. 29, the bone plate 1002 includes a cutout 1040 between the jaws 1008 that enhances the flexibility of the jaws 1008. The jaws 1008 may be compressed in different amounts depending on patient geometry. The bone plate 1002 thereby provides greater flexibility than some bone plates which require uniform deformation of the plate along the entire length of the plate.

Figure 29A:
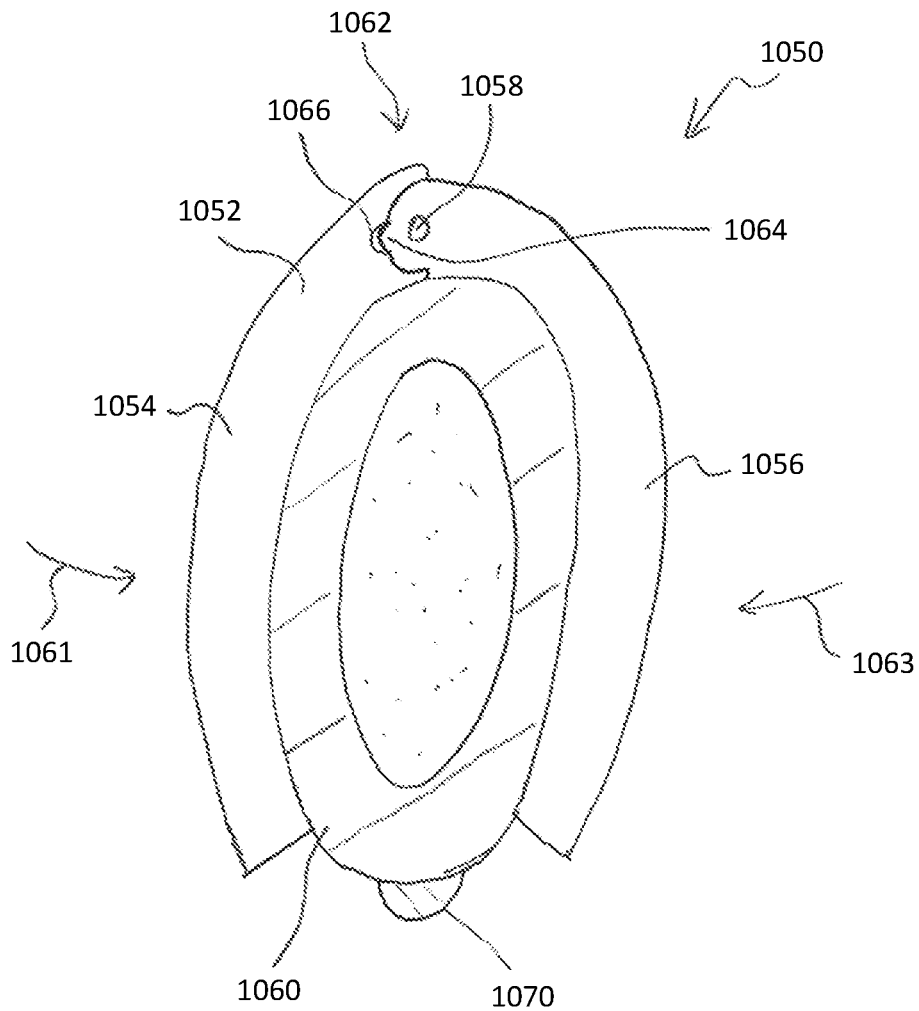
FIG. 29A is a side elevational view of another bone plate system including a bone plate having a hinge and locking device.
Figure 30:
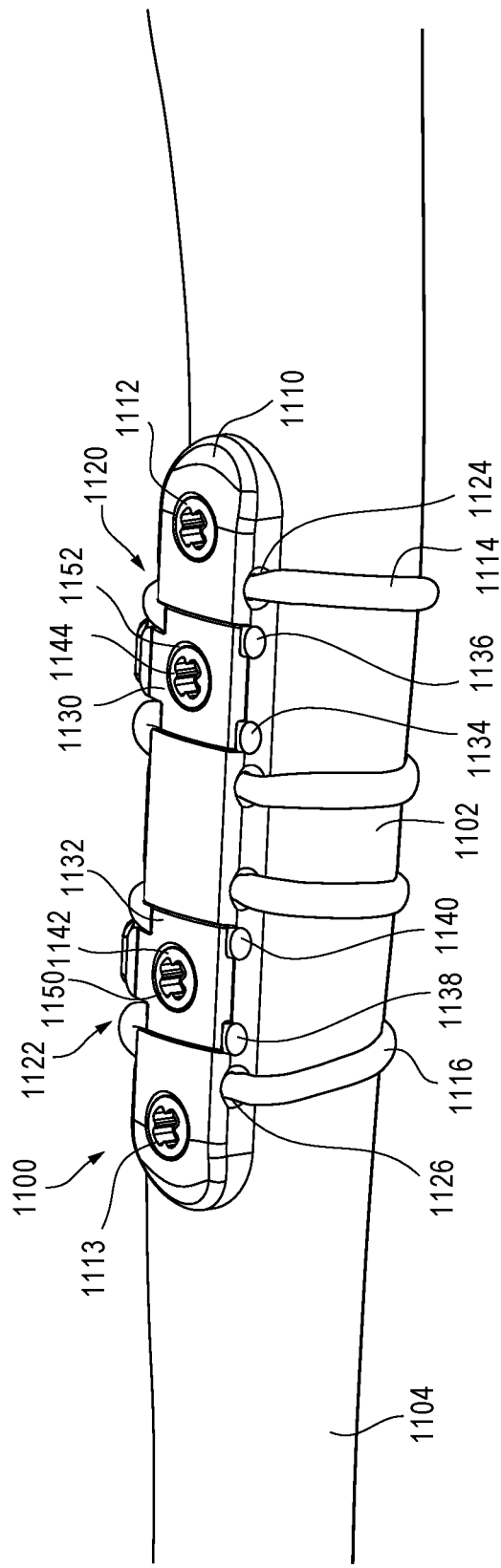
FIG. 30 is a perspective view of another bone plate system showing the bone plate system stabilizing portions of a broken clavicle bone.

With reference to FIG. 29A, another bone plate system 1050 is shown that is similar in many respects to the bone plate system 1000 such that differences between the two will be highlighted. One difference between the bone plate systems 1000, 1050 is that the bone plate system 1050 includes a bone plate 1052 having two jaws 1054, 1056 and a hinge 1058 pivotally connecting the jaws 1054, 1056. Rather than utilize the resilient properties of the bone plate 1052 to cause the jaws 1054, 1056 to clamp a cut rib 1060, the bone plate 1052 has a locking device 1062 configured to hold the jaws 1054, 1056 in a clamping configuration about the cut rib 1060 once the jaws 1054, 1056 have been compressed in directions 1061, 1063 against the cut rib 1060. In one form, the locking device 1062 includes a protrusion 1064 of the jaw 1056 that snaps into a recess 1066 of the jaw 1054 once the jaws 1054, 1056 have been pivoted toward each other about the hinge 1058 to a predetermined clamping configuration. The engagement of the protrusion 1064 and recess 1066 restricts relative pivoting movement of the jaws 1054, 1056 about the hinge 1058 and maintains the jaws 1054, 1056 in the clamping configuration thereof. With reference to FIG. 29A, it will be appreciated that jaws 1054, 1056 are configured to avoid interference with a neurovascular bundle 1070 running along an underside of the cut rib 1060.

With reference to FIGS. 30-41, another bone plate system 1100 is shown. The bone plate system 1100 is especially well suited for stabilizing bone portions, such as portions 1104, 1106 of clavicle bone separated by a break or cut 1102. The bone plate system 1100 includes a bone plate 1110 having bone screws 1112, 1113, 1142, 1144 that provide primary fixation system for securing the bone plate 1110 to the bone portions 1104, 1106 and surgical cables 1114, 116 that provide a secondary fixation system for securing the bone plate 1110 to the bone portions 1104, 1106.

The bone plate 1110 includes locking mechanisms 1120, 1122 and tortuous pathways 1124, 1126 for securing the cables 1114, 1116 to the bone plate 1110. The locking mechanisms 1120, 1122 and tortuous pathways 1124, 1126 are particularly well suited to secure polymer surgical cables 1114, 1116 to the bone plate 1110. Polymer surgical cables 1114, 1116 may be desirable in some applications because the cables 1114, 1116 tend to flatten out against the bones 1106, 1104 rather than biting into the bone portions 1104, 1106. Further, ends of the polymer cables 1114, 1116 generally do not fray after cutting which may occur with metal surgical cables. With continued reference to FIG. 30, the locking mechanisms 1120, 1122 include clamp bodies 1130, 1132 that are drawn toward the bone plate 1110 against end portions 1134, 1136, 1138, 1140 of the cables 114, 116 by driving the bone screws 1142, 1144 into throughbores 1150, 1152 of the bone plate 1110.

Figure 31:
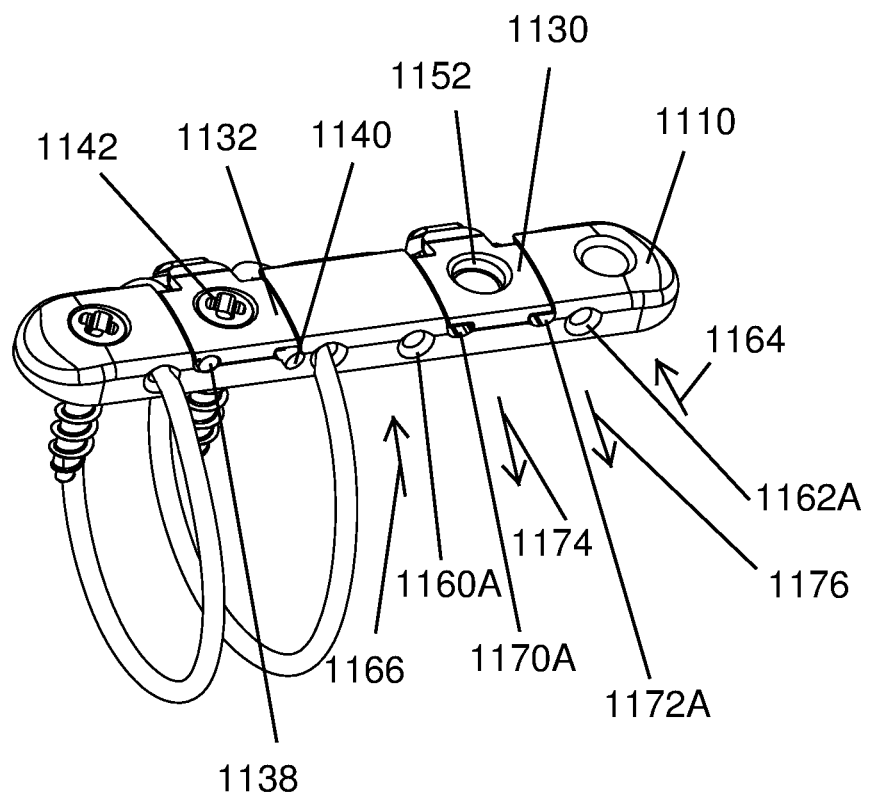
FIG. 31 is a perspective view of the bone plate system of FIG. 30 showing two bone anchors and a cable of the bone plate system removed.
Figure 32:
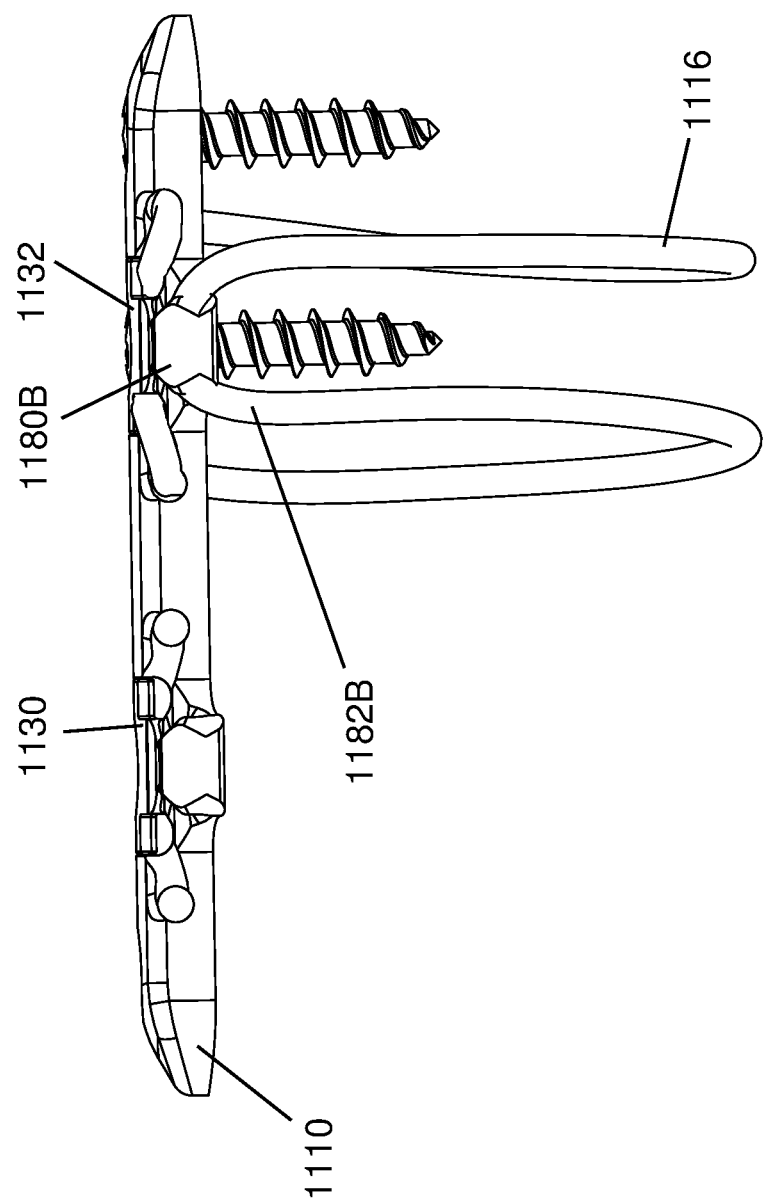
FIG. 32 is a front elevational view of the bone plate of FIG. 31 showing a cable of the bone plate system looped around a seat of the bone plate.
Figure 33:
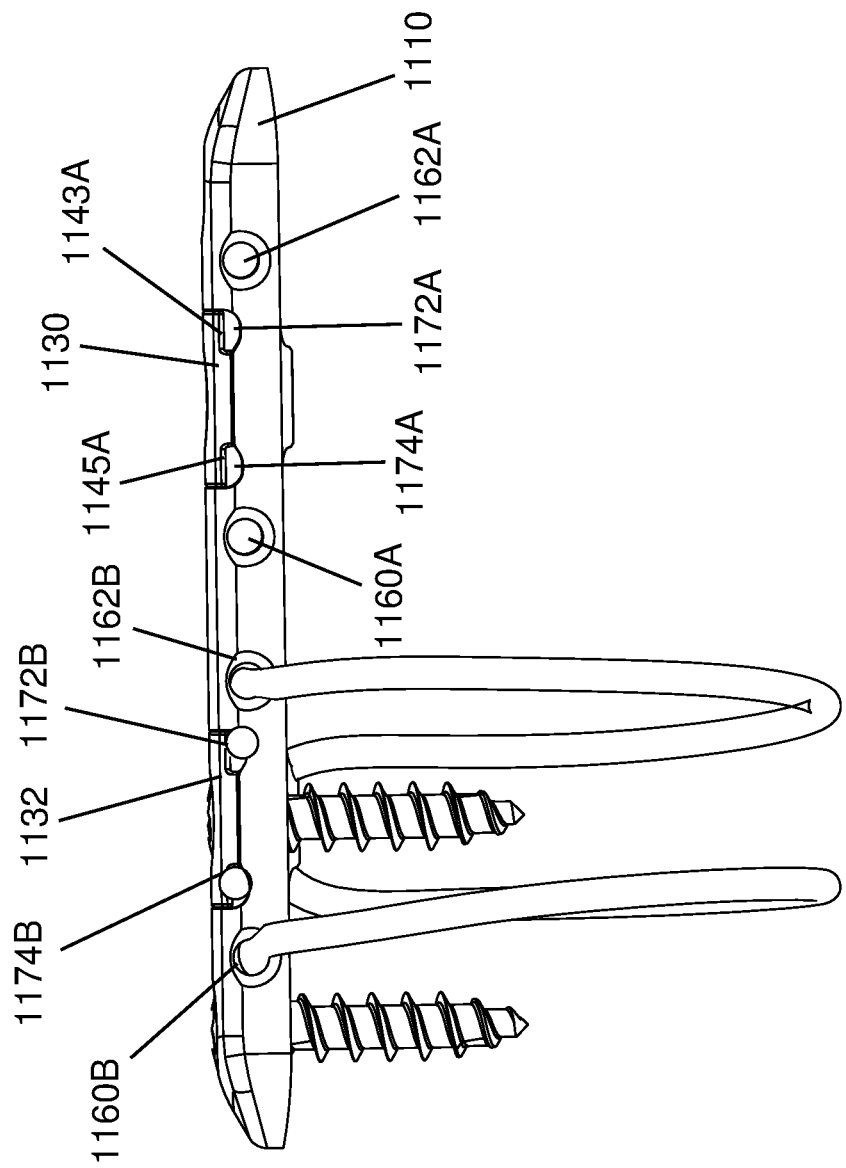
FIG. 33 is a rear elevational view of the bone plate of FIG. 31 showing lengths of the cable extending outward from openings of the bone plate.
Figure 34:
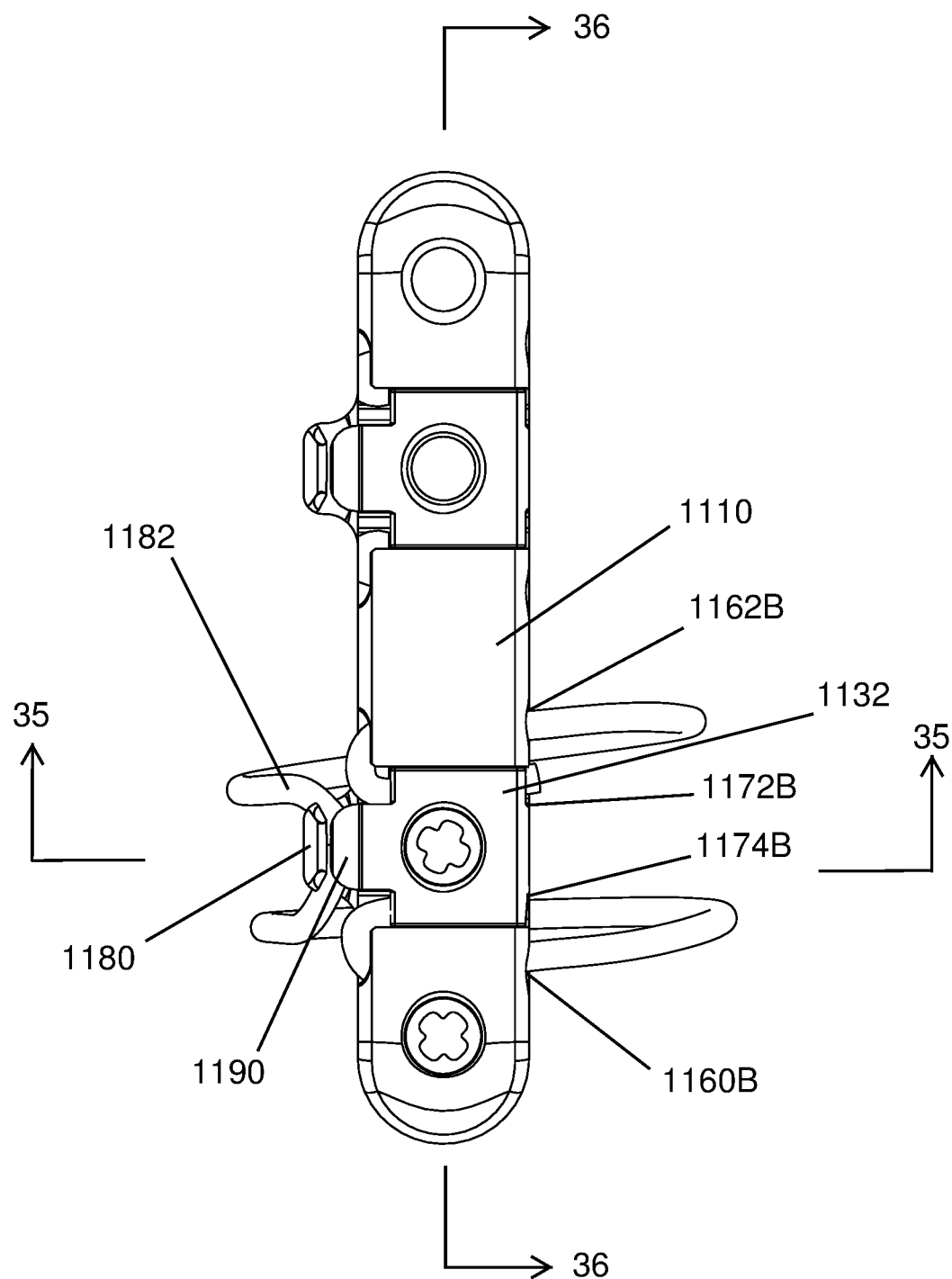
FIG. 34 is a top plan view of the bone plate of FIG. 31 showing a clamp body holding end portions of the cable and the loop of the cable against the bone plate.
Figure 35:
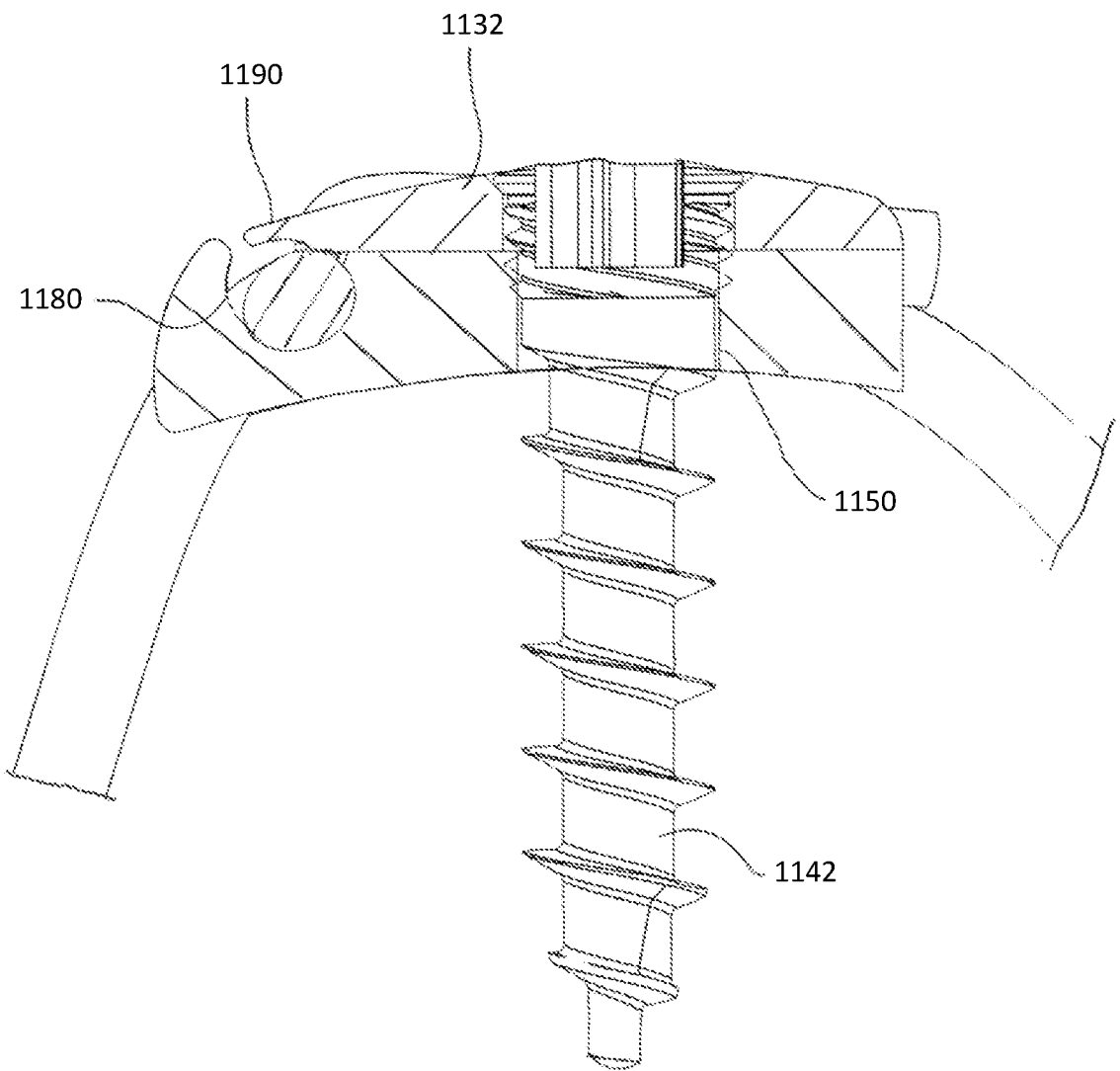
FIG. 35 is a cross-sectional view taken across line 35-35 in FIG. 34 showing an arm of the clamp body capturing the loop of the cable on the bone plate seat.
Figure 36:
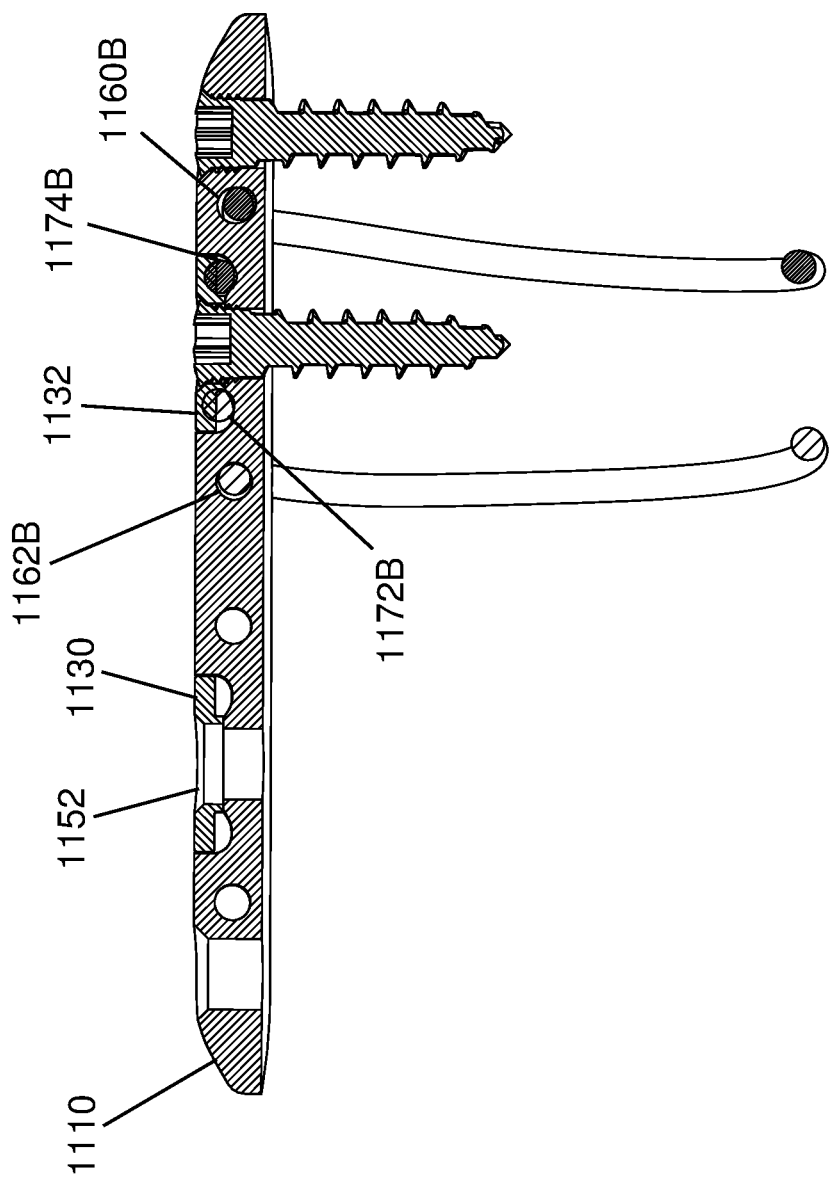
FIG. 36 is a cross-sectional view taken across line 36-36 in FIG. 34 showing the clamp body clamping end portions of the cable against the bone plate.
Figure 37:
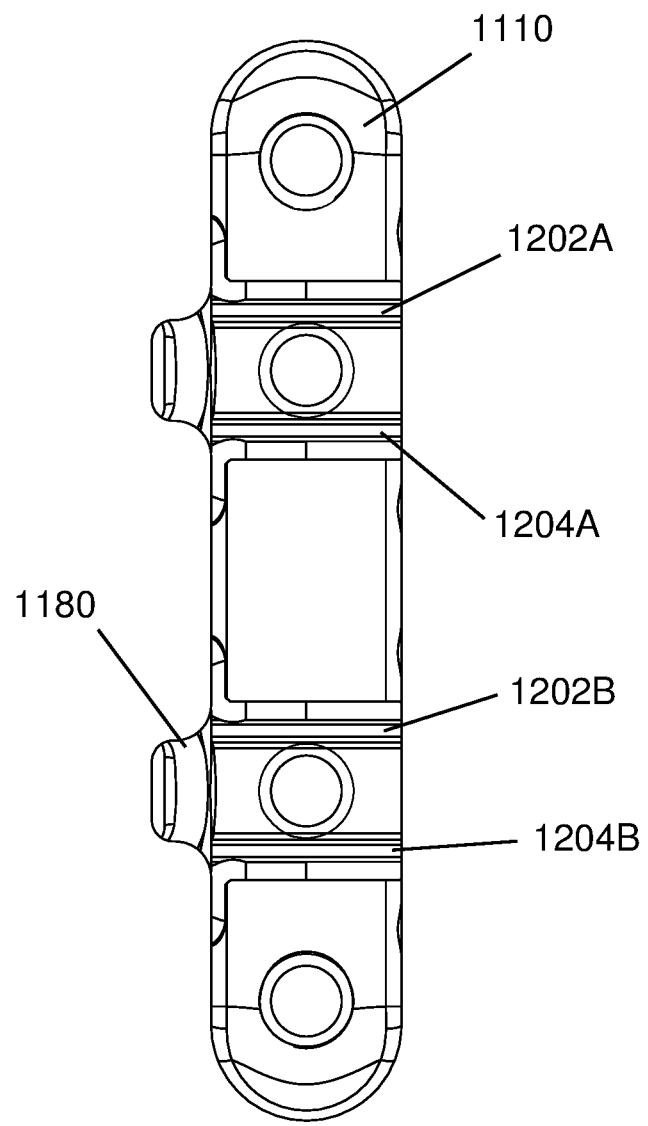
FIG. 37 is a top plan view of the bone plate of FIG. 30 showing recesses of the bone plate configured to receive the clamp bodies.

With reference to FIGS. 31-33, the bone plate 1112 is shown with the bone screw 1144 and the cable 1114 removed. The bone plate 1112 has a pair of lateral inlet through openings 1160A, 1162A through which end portions 1134, 1136 of the cable 1114 are advanced in directions 1164, 1166, as discussed in greater detail below. The bone plate 1112 also has lateral outlet through openings 1170A, 1172A through which the cable end portions 1134, 1136 are advanced outwardly therefrom in directions 1174, 1176.

With reference to FIG. 32, the bone plate 1112 has a seat 1180B that supports a loop 1182B of the cable 1116. The clamp body 1132 has an arm 1190 that captures the cable loop 1182B against the seat 1180B when the bone screw 1142 is driven into the throughbore 1150 and clamps the clamp body 1132 against the cable end portions 1138, 1140.

Figure 38:
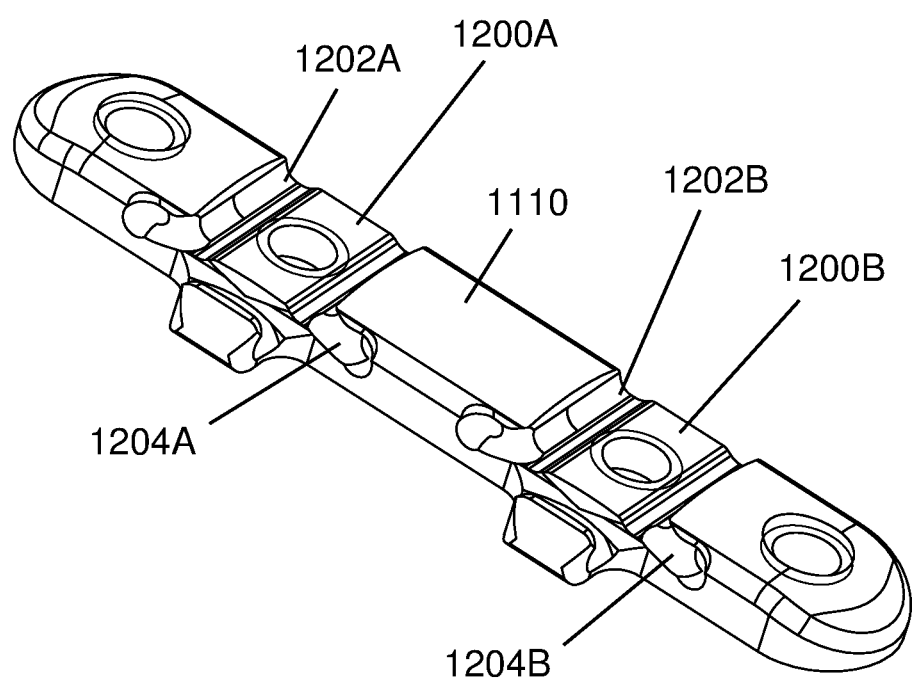
FIG. 38 is a perspective view of the bone plate of FIG. 30 showing grooves of the bone plate recesses for receiving end portions of the cables below the clamp bodies.

With reference to FIG. 38, the bone plate 1112 has recess 1200A, 1200B sized to receive the clamp bodies 1130, 1132 and grooves 1202A, 1204A and 1202B, 1204B configured to receive the end portions 1134, 1136 of the cable 1114 and end portions 1138, 1140 of the cable 1116.

Figure 39:
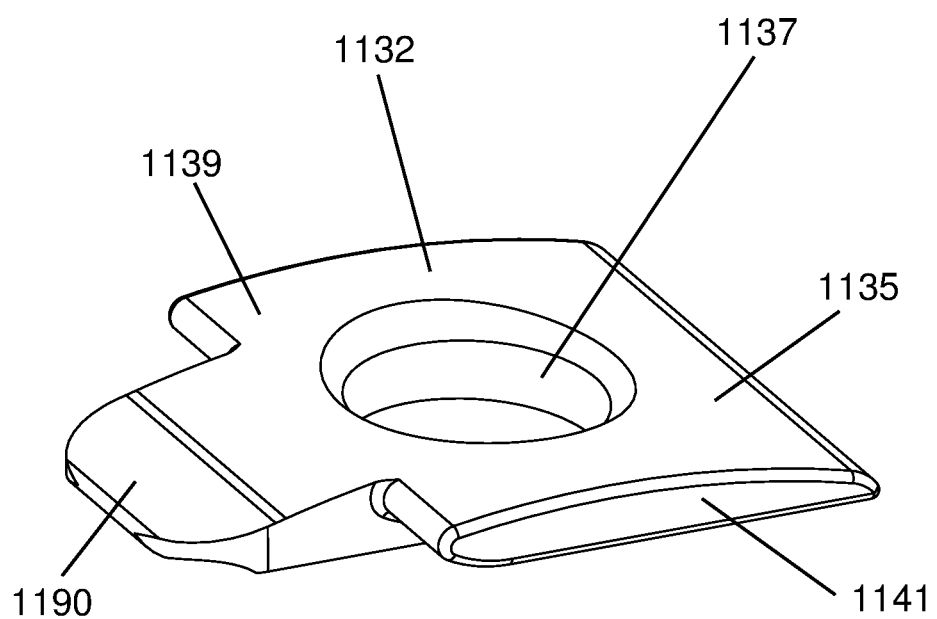
FIG. 39 is a perspective view of one of the clamp bodies of the bone plate of FIG. 30 showing clamping members of the clamp body.
Figure 40:
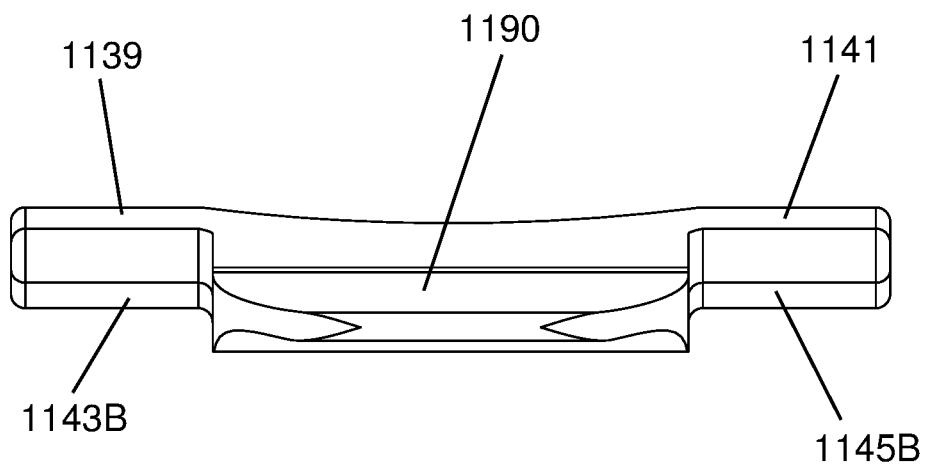
FIG. 40 is a front elevational view of the clamp body of FIG. 39 showing the clamping members extending outward from a body portion of the clamp body.
Figure 41:
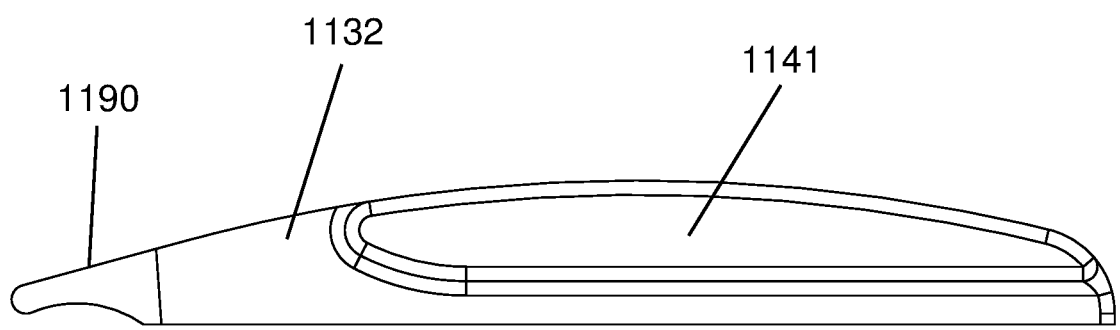
FIG. 41 is a side elevational view of the clamp body of FIG. 39 showing a concave lower surface of the clamp body arm.

With reference to FIGS. 39-41, the clamp body 1132 has a body portion 1135 with a clamp body section 1137 of the throughbore 1152 and clamping members 1139, 1141 extending laterally outwardly from the body portion 1135. The clamping members 1139, 1141 form a step profile of the clamp body 1132, as shown in FIG. 40. Further, the clamping members 1139, 1141 have lower surfaces 1143, 1145 that rest upon the cable end portions 1138, 1140 and clamp the cable end portions 1138, 1140 between the clamp body 1132 and the bone plate 1110.

With reference to FIGS. 42-46, a method of securing the bone plate system 1100 to the bone portions 1104, 1106 is shown. Initially, the bone plate 1110 is positioned against the bone portions 1104, 1106 and screws 1112, 1113 are driven into the respective throughbores to secure the bone plate 1110 to the bone portions 1104, 1106. In another approach, the bone screws 1112, 1113 may be applied after the cables 1114, 1116 have been used to secure the plate 1110 to the bone portions 1104, 1106.

Figure 42:
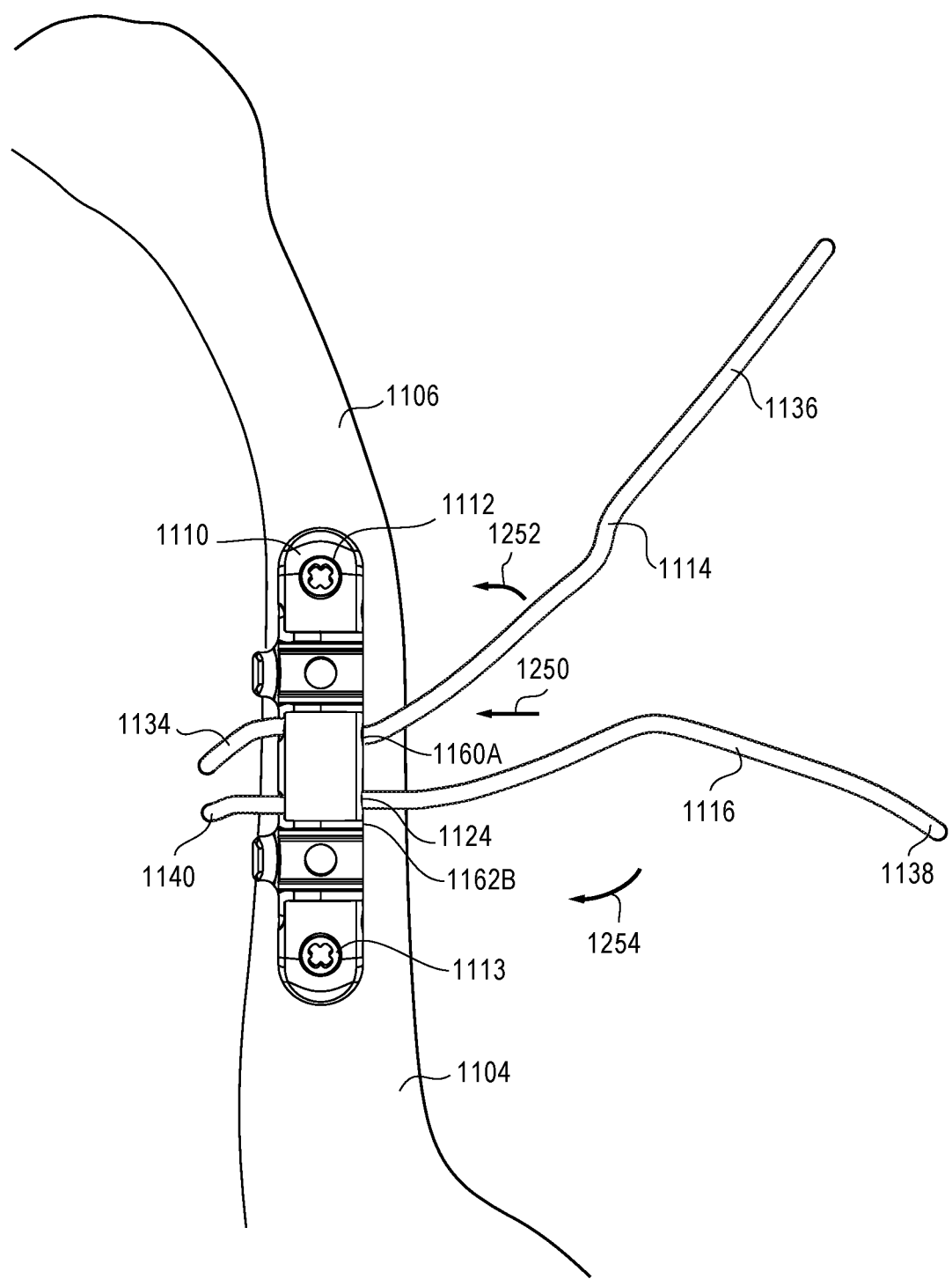
FIGS. 42-46 are schematic views of a method of securing the bone plate system of FIG. 30 to portions of a cut clavicle bone.

With reference to FIG. 42, the end portions 1134, 1140 of the cables 1114, 1116 are advanced through the inlet openings 1162B in direction 1250 until the end portions 1134, 1140 extend outward from a lateral side of the bone plate 1110. In another approach, the cables 1114, 1116 may be preassembled to the bone plate 1110 that the end portions 1134, 1140 are already extending laterally from the bone plate 1110 as the bone plate system 1100 is shipped from the manufacturing facility. Next, the end portions 1136, 1138 are looped behind the bone portions 1104, 1106 in directions 1252, 1254 which moves the end portions 1136, 1138 from one side of the bone plate 1110 to the other.

Figure 43:
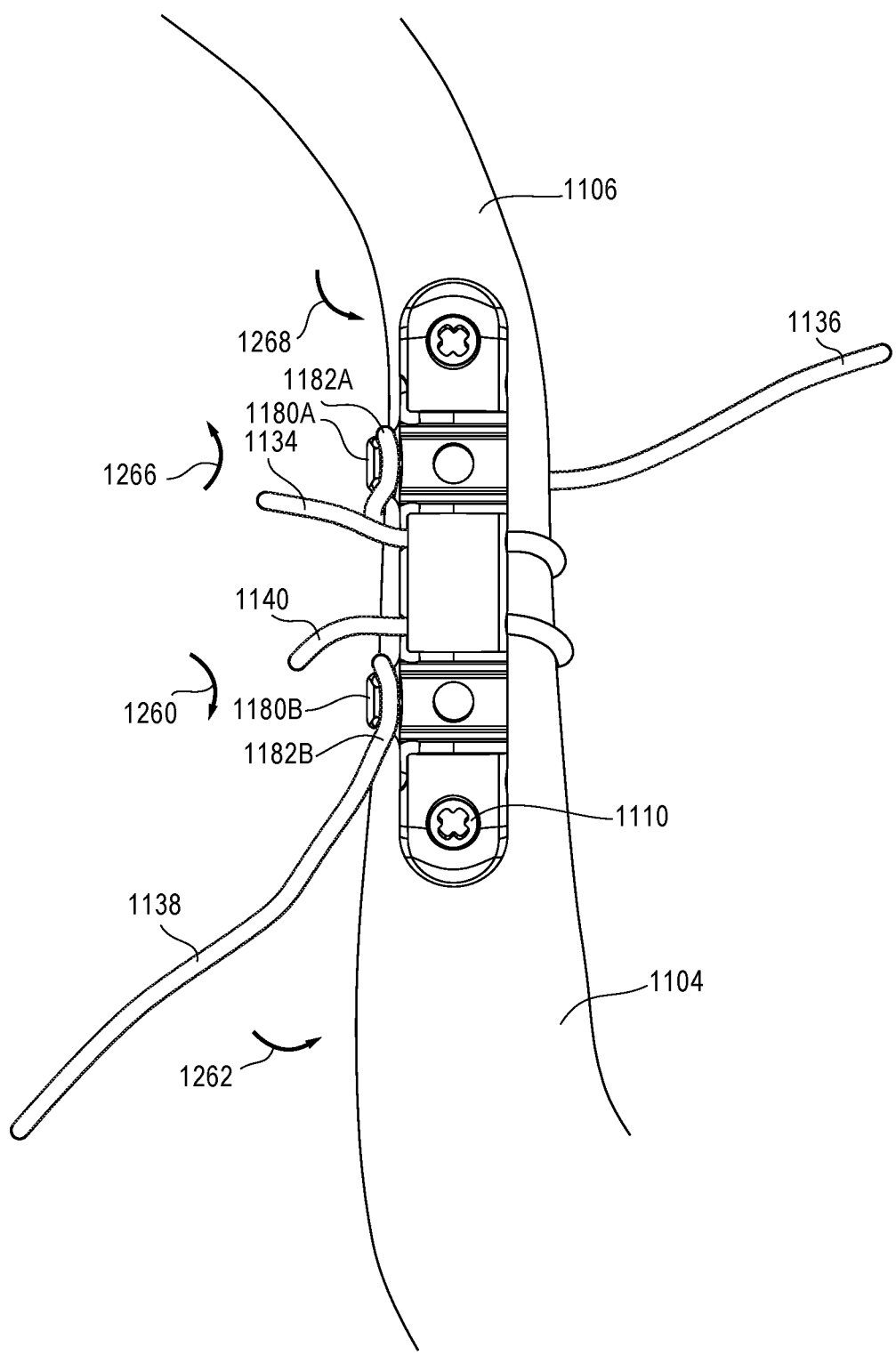

With reference to FIG. 43, the cable end portion 1138 is then looped in direction 1260 over the seat 1180B of the bone plate 1110 to form the loop 1182B before the end portion 1138 is advanced in direction 1262 behind the bone portion 1104 back toward the position of the end portion 1138 shown in FIG. 42. The cable end portion 1136 is then looped around the seat 1180A in direction 1266 to form loop 1182A before the end portion 1136 is advanced behind the bone portion 1106 back to the other side of the bone plate 1110 in direction 1268, as shown in FIG. 43.

Figure 44:
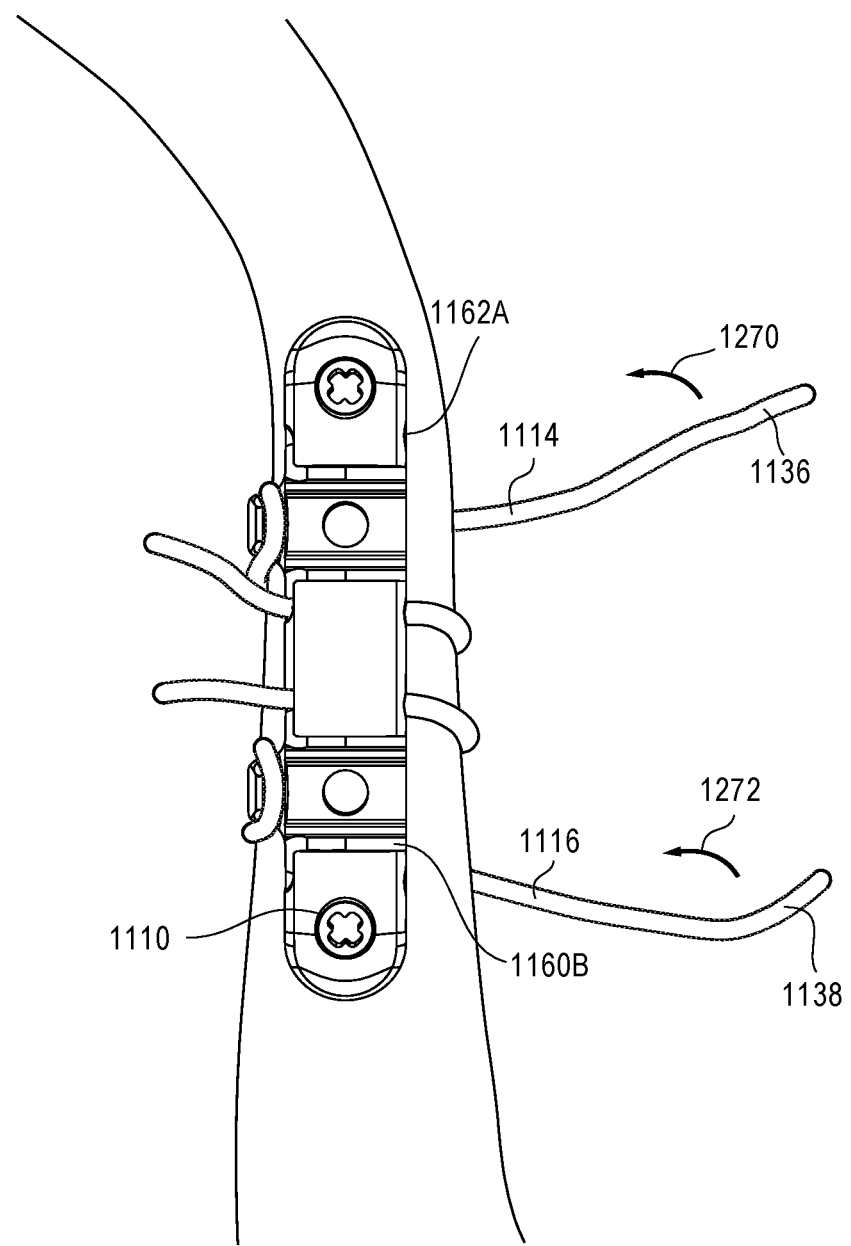
Figure 45:
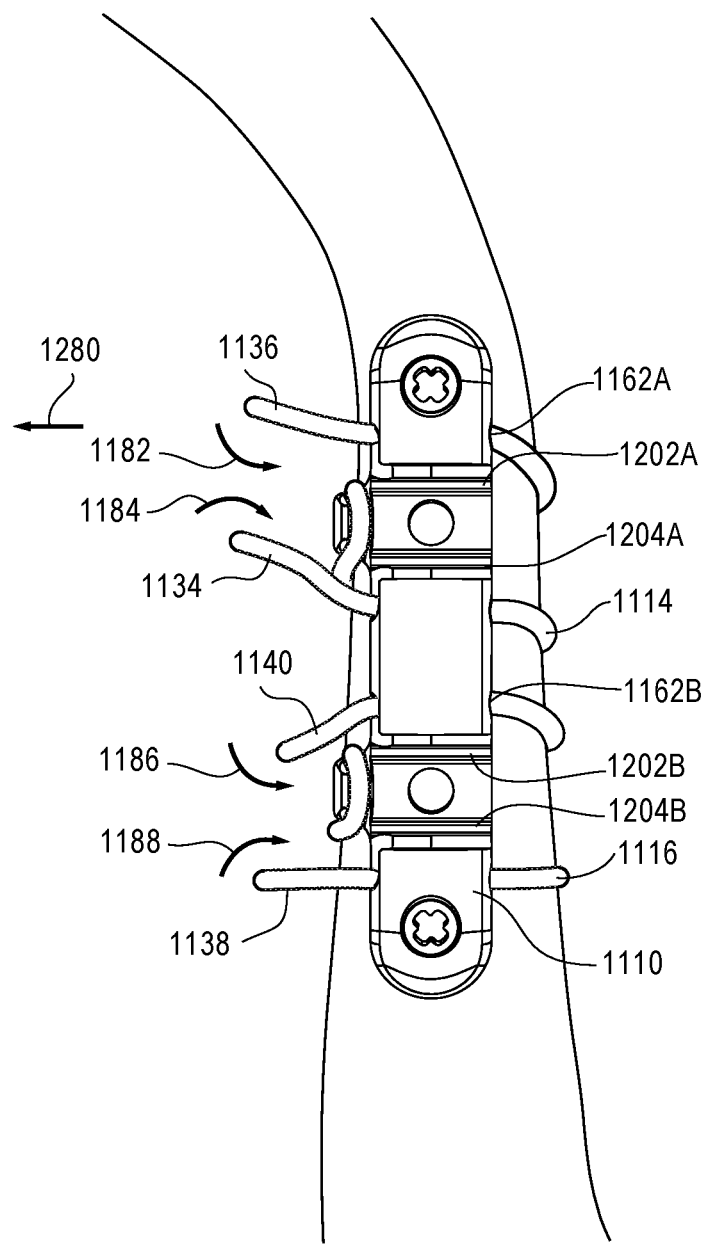
Figure 46:
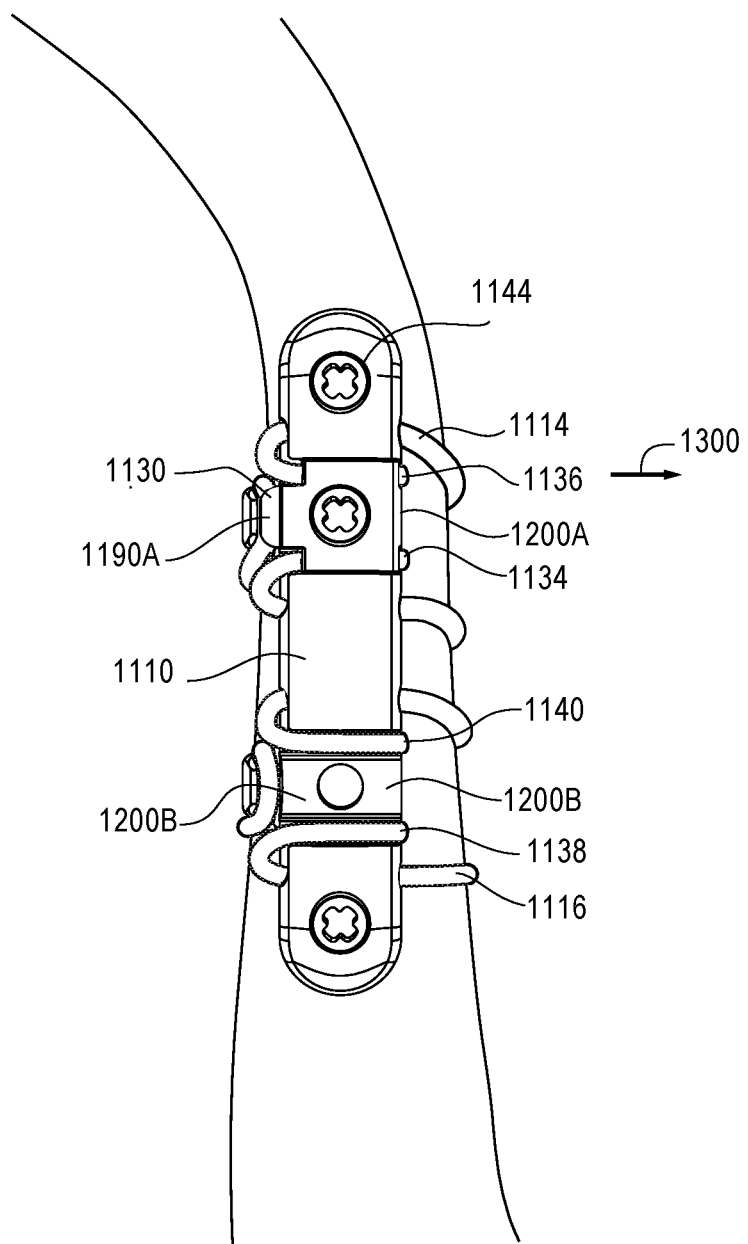

With reference to FIG. 44, the cable end portions 1136, 1138 are then advanced in directions 1270, 1272 into and along the inlet lateral through openings 1162A, 1160B (see FIG. 33). With reference to FIG. 45, the cable end portions 1134, 1136, 1138, 1140 are all extending outward from the bone plate 1110 and may be pulled in directions 1280 or otherwise adjusted to remove slack from the cables 1114, 1116. Once substantially all the slack has been removed from the cables 1114, 1116, the end portions 1134, 1136 are folded inward in directions 1182, 1184 and positioned along the grooves 1202A, 1204A, and the cable end portions 1138, 1140 are also folded inward in directions 1186, 1188 to position the end portions 1138, 1140 in the grooves 1202B, 1202B With reference to FIG. 46, the clamp body 1130 is positioned in the recess 1200a to position the clamp surfaces 1143A, 1145A of the clamp body 1130 (see FIG. 33) onto the cable end portions 1134, 1136. The screw 1144 may be partially driven into the throughbore 1152 in order to temporarily restrain the clamp body 1130 on the bone plate 1110. The cable ends 1134, 1136 may then be pulled in direction 1300 to apply tension to the cable 1114 and draw any remaining slack outward therefrom. The screw 1144 may then be fully driven further into the throughbore 1152.

This draws the clamp body 1130 and clamp surfaces 1143A, 1145A thereof firmly against the cable end portions 1134, 1136 and clamps the cable end portions 1134, 1136 between the clamp body 1130 and the bone plate 1110. In this manner, the cable 1114 is fixed to the bone plate 1110 secures the bone plate 1110 to the bone portion 1106. A similar process is repeated with the clamp body 1132 in order to tension the cable 1116 and clamp the cable end portions 1138, 1140 between the clamp body 1132 and the bone plate 1110.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. A bone plate system comprising:
    a surgical cable having opposite end portions and an intermediate portion intermediate the end portions along the surgical cable, the intermediate portion of the surgical cable configured to extend around at least one bone;
    a bone plate having a plurality of throughbores and a pair of cable-receiving portions adjacent one of the throughbores configured to receive the end portions of the surgical cable;
    bone screws for being driven into the throughbores and engaging the at least one bone;
    a clamp body having a through opening for being oriented in communication with the one throughbore of the bone plate, the clamp body having clamping surfaces for clamping the cable end portions between the clamp body clamping surfaces and the cable-receiving portions of the bone plate;
    the through opening of the clamp body sized to receive one of the bone screws to allow the bone screw to be driven through the through opening of the clamp body and the one throughbore of the bone plate and into the at least one bone for securing the bone plate to the at least one bone, fastening the clamp body to the bone plate, and clamping the cable end portions between the clamp body clamping surfaces and the cable-receiving portions of the bone plate.

2. A bone plate system comprising:
    a surgical cable configured to extend around at least one bone;
    a bone plate having a plurality of throughbores and a cable-receiving portion adjacent one of the throughbores configured to receive a portion of the surgical cable;
    bone screws for being driven into the throughbores and engaging the at least one bone;
    a clamp body for clamping the cable portion between the clamp body and the cable-receiving portion of the bone plate;
    a through opening of the clamp body for being oriented in communication with the one throughbore of the bone plate and sized to receive one of the bone screws to allow the bone screw to be driven through the through opening of the clamp body and the one throughbore of the bone plate and into the at least one bone for securing the bone plate to the at least one bone, fastening the clamp body to the bone plate, and clamping the cable portion between the clamp body and the cable-receiving portion of the bone plate;
    wherein the surgical cable includes a pair of opposite end portions, the bone plate cable-receiving portion includes a pair of cable-receiving portions adjacent the one throughbore configured to receive the end portions of the surgical cable, and the clamp body includes a pair of clamping members configured to clamp the cable end portions between the clamping members and the cable-receiving portions of the bone plate;

wherein the clamp body includes a lowermost bottom surface extending about the through opening, lower surfaces of the clamping members which contact the cable end portions, and side surfaces extending vertically between the lowermost bottom surface and the lower surfaces of the clamping members.

3. The bone plate system of claim 1 wherein the bone plate includes a pair of straight walls defining a recess therebetween sized to receive the clamp body and the clamp body includes flat sides abutting the straight walls of the bone plate.

4. The bone plate system of claim 1 wherein at least one of the cable-receiving portions of the bone plate includes a groove.

5. The bone plate system of claim 4 wherein the groove is L-shaped and includes a first portion extending along the bone plate and a second portion extending across the bone plate.

6. The bone plate system of claim 1 wherein the bone plate includes:
a lower surface for being placed against a bone, an upper surface opposite the lower surface, and side surfaces extending between the upper and lower surfaces; and
a lateral throughbore extending intermediate the side surfaces sized to receive a length of the surgical cable.

7. The bone plate system of claim 1 wherein the clamp body includes a wall extending about the throughbore and including threads and the one bone screw includes a head having threads configured to engage the threads of the clamp body.

8. The bone plate system of claim 1 wherein the surgical cable is a polymer cable.

9. A bone plate system comprising:
a surgical cable configured to be looped around a bone, the surgical cable having a pair of opposite end portions and an intermediate portion;
a plurality of bone screws;
a bone plate having a lower surface for being placed against the bone, an upper surface opposite the lower surface, and side walls extending between the upper and lower surfaces;
throughbores of the bone plate for receiving the bone screws;
a pair of through openings of the bone plate extending laterally between the side walls and opening thereto, the through openings sized to permit the cable to be advanced therethrough so that one of the end portions projects outwardly from one of the through openings;
a cable bending portion of the bone plate adjacent the one through opening that is configured to permit bending of the cable about the cable bending portion so that the cable bending portion contacts the cable between the one end portion of the cable and the intermediate portion of the cable with the cable extending in the one through opening;
a hook of the bone plate adjacent one of the side walls configured to support the intermediate portion of the cable; and
a clamp operable to secure the one end portion of the surgical cable to the bone plate so that with the surgical cable extending around the bone the surgical cable includes a length extending from the hook, around the bone, and to the clamp.

10. The bone plate system of claim 9 wherein the through openings are sized to permit the cable to be advanced therethrough so that a second one of the end portions of the cable projects outwardly from a second one of the through openings;
a second cable bending portion of the bone plate adjacent the second through opening and configured to permit bending of the cable about the second cable bending portion so that the second cable bending portion contacts the cable between the second end portion and the intermediate portion of the cable;
wherein the clamp is operable to secure both of the end portions of the surgical cable to the bone plate so that with the surgical cable extending around the bone the surgical cable includes a pair of lengths extending from the hook, around the bone, and to the clamp.

11. The bone plate system of claim 9 wherein the clamp includes a clamp body that is connectable to the bone plate for clamping the one end portion of the surgical cable between the clamp body and the bone plate.

12. A bone plate system comprising:
a surgical cable configured to be looped around a bone, the surgical cable having a pair of opposite end portions and an intermediate portion;
a plurality of bone screws;
a bone plate having a lower surface for being placed against the bone, an upper surface opposite the lower surface, and side walls extending between the upper and lower surfaces;
throughbores of the bone plate for receiving the bone screws;
a pair of through openings of the bone plate extending laterally between the side walls and opening thereto, the through openings sized to permit the end portions of the cable to be advanced therethrough;
a hook of the bone plate adjacent one of the side walls configured to support the intermediate portion of the cable;
a clamp operable to secure at least one of the end portions of the surgical cable to the bone plate so that with the surgical cable extending around the bone the surgical cable includes a length extending from the hook, around the bone, and to the clamp;
wherein the clamp includes a clamp body that is connectable to the bone plate and includes an arm that extends above the hook of the bone plate with the clamp body connected to the bone plate to capture the surgical cable intermediate portion between the arm and the hook.

13. The bone plate system of claim 9 wherein the clamp includes a clamp body that is removable from the bone plate, the clamp body having a through opening for being oriented in communication with one of the throughbores of the bone plate and sized to receive one of the bone screws.

14. The bone plate system of claim 9 wherein the clamp includes a clamp body that is connectable to the bone plate, the connected clamp body and the bone plate defining therebetween a second pair of through openings extending laterally between the side walls of the bone plate sized to receive the surgical cable end portions.

15. The bone plate system of claim 9 wherein the bone plate is elongated and the hook of the bone plate is located along the bone plate intermediate the through openings of the bone plate.

16. A bone plate system comprising:
a surgical cable configured to be looped around a bone, the surgical cable having a pair of opposite end portions and an intermediate portion;
a plurality of bone screws;
a bone plate having a lower surface for being placed against the bone, an upper surface opposite the lower surface, and side walls extending between the upper and lower surfaces;
throughbores of the bone plate for receiving the bone screws;
a pair of through openings of the bone plate extending laterally between the side walls and opening thereto, the through openings sized to permit the end portions of the cable to be advanced therethrough;
a hook of the bone plate adjacent one of the side walls configured to support the intermediate portion of the cable; and
a clamp operable to secure at least one of the end portions of the surgical cable to the bone plate so that with the surgical cable extending around the bone the surgical cable includes a length extending from the hook, around the bone, and to the clamp;
a pair of recesses for receiving the surgical cable end portions after the surgical cable end portions have been advanced through the through openings of the bone plate; and
a pair of walls each separating one of the recesses from one of the through openings, the walls permitting the surgical cable to be bent around the walls to resist movement of the surgical cable relative to the bone plate.

17. The bone plate system of claim 16 wherein the walls include grooves connecting the through openings and the recesses.

18. The bone plate system of claim 9 wherein the bone plate has a unitary, one-piece construction.

19. The bone plate system of claim 9 wherein the surgical cable is a polymer surgical cable.

20. The bone plate system of claim 1 wherein the surgical cable is a metal cable.

21. The bone plate system of claim 9 wherein the surgical cable is a metal cable.

22. The bone plate system of claim 1 wherein the cable-receiving portions of the bone plate are on opposite sides of the one throughbore of the bone plate and the clamping surfaces of the clamp body are on opposite sides of the through opening of the clamp body.

23. The bone plate system of claim 9 wherein the cable bending portions includes a wall portion of the bone plate.

24. The bone plate system of claim 9 wherein the through openings permit the cable to be advanced therethrough so that both of the end portions project outwardly from the through openings at one side wall of the bone plate; and
wherein the hook is adjacent the through openings of the bone plate.

25. The bone plate system of claim 24 further comprising a second cable bending portion of the bone plate, wherein each cable bending portion is adjacent a different one of the through openings of the bone plate; and
wherein the hook is longitudinally intermediate the cable bending portions along the bone plate.

26. The bone plate system of claim 9 wherein the clamp includes a clamp body distinct from the bone plate for clamping the one end portion of the cable between the clamp body and the bone plate.

* * * * *